US006564103B2

(12) United States Patent
Fischer et al.

(10) Patent No.: US 6,564,103 B2
(45) Date of Patent: May 13, 2003

(54) ELECTRICAL STIMULATOR AND METHOD OF USE

(75) Inventors: Wallace Ray Fischer, Amesville, OH (US); Raymond Charles Fischer, Amesville, OH (US)

(73) Assignee: VisionQuest Industries, Inc., Irvine, CA (US)

( * ) Notice: Subject to any disclaimer, the term of this patent is extended or adjusted under 35 U.S.C. 154(b) by 249 days.

(21) Appl. No.: 09/728,925

(22) Filed: Dec. 1, 2000

(65) Prior Publication Data

US 2002/0068961 A1 Jun. 6, 2002

(51) Int. Cl.[7] .................................................. A61N 1/08
(52) U.S. Cl. .............................. 607/59; 607/72; 607/67
(58) Field of Search .............................. 607/59, 63, 64, 607/66, 67, 72, 62

(56) References Cited

U.S. PATENT DOCUMENTS

| 4,144,893 A | 3/1979 | Hickey |
| 4,177,819 A | 12/1979 | Kofsky et al. |
| 4,324,253 A | 4/1982 | Greene et al. |
| 4,392,496 A | 7/1983 | Stanton |
| RE32,091 E | 3/1986 | Stanton |
| 4,690,146 A | 9/1987 | Alon |
| 4,832,033 A | * 5/1989 | Maher et al. ................. 607/48 |
| 4,887,603 A | 12/1989 | Morawetz |
| 4,926,865 A | 5/1990 | Oman |
| 4,977,895 A | 12/1990 | Tannenbaum |
| 4,989,605 A | 2/1991 | Rossen |
| 5,010,896 A | 4/1991 | Westbrook |
| 5,048,523 A | 9/1991 | Yamasawa |
| 5,269,304 A | 12/1993 | Matthews |
| 5,514,165 A | 5/1996 | Malaugh et al. |
| 5,776,171 A | 7/1998 | Peckham et al. |
| 5,800,458 A | 9/1998 | Wingrove |
| 6,064,911 A | 5/2000 | Wingrove |
| 6,393,328 B1 | * 5/2002 | McGraw et al. .............. 607/67 |

* cited by examiner

Primary Examiner—Mark Bockelman
(74) Attorney, Agent, or Firm—Stetina Brunda Garred & Brucker

(57) ABSTRACT

A system and method for performing multiple modes of electro-therapy with a portable electro-therapy device are disclosed. Preferably, the modes include an interferential mode, a pre-modulated interferential mode, a neuromuscular mode and a high volt pulse current mode. Additional protocols may be defined by combining or varying modes. The electro-therapy device uses a microprocessor to generate and control output signals. The microprocessor is contained within the housing of the electro-therapy device. The device includes a display and at least one keypad. The device also includes an electrode jack for attaching at least one pair of electrodes for outputting signals to a patient.

26 Claims, 19 Drawing Sheets

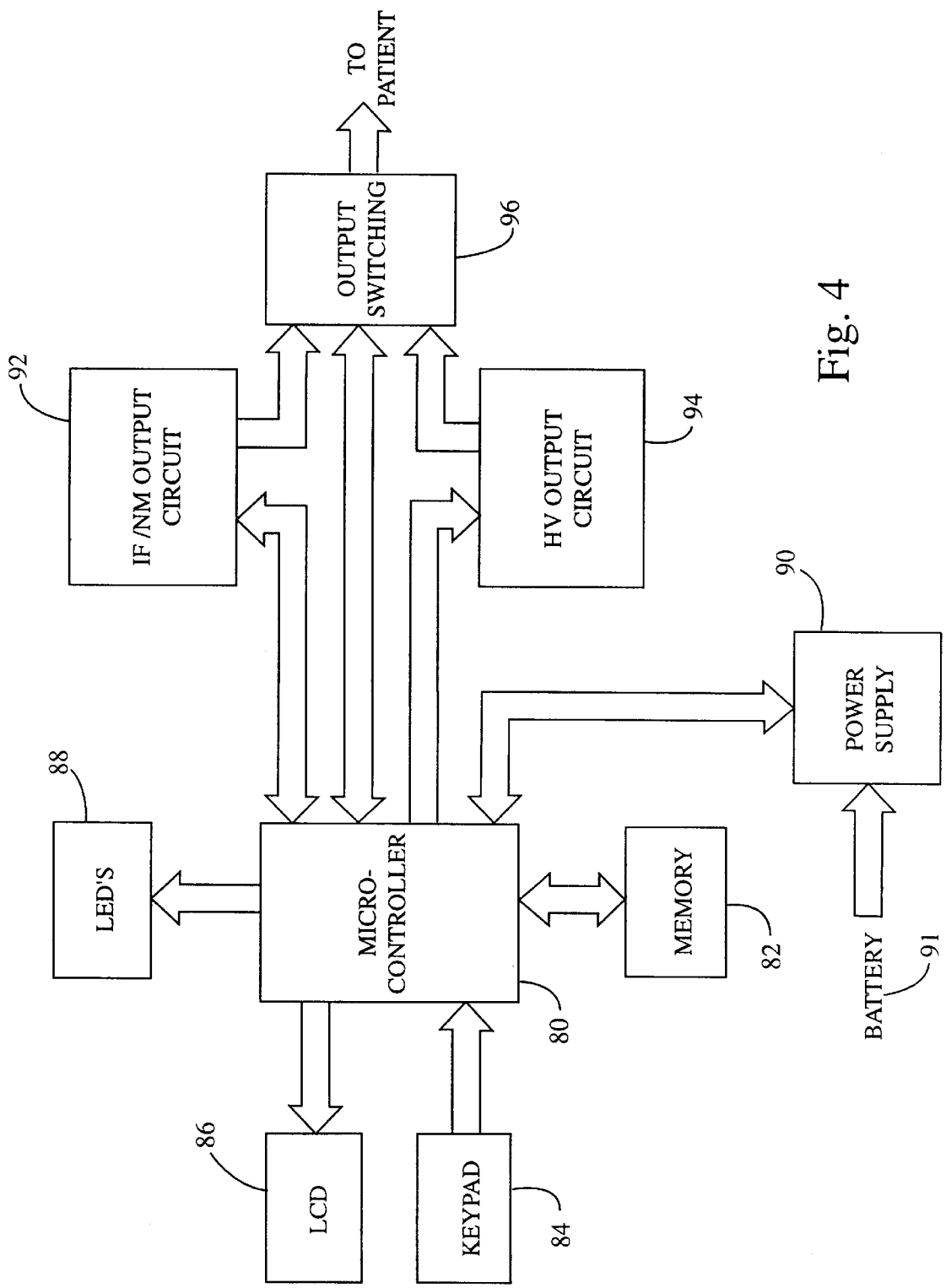

SHIFT

ELECTRICAL STIMULATOR AND METHOD OF USE

CROSS-REFERENCE TO RELATED APPLICATIONS (Not Applicable)

STATEMENT RE: FEDERALLY SPONSORED RESEARCH/DEVELOPMENT (Not Applicable)

BACKGROUND OF THE INVENTION

The present invention generally relates to electro-therapy devices and more particularly to a portable multi-function electro-therapy device which uses a microprocessor to generate and control output signals.

The therapeutic use of electricity (also known as electro-therapy) is known. Electricity can be used, for example, to reduce pain (U.S. Pat. No. 4,887,603 issued to Morawitz et al.) or for treating edema, muscle spasms, and sprains (U.S. Pat. No. 5,010,896 issued to Westbrook). There are a variety of forms of electrical therapy as described more fully below.

Transcutaneous Electrical Nerve Stimulation (TENS) generates electrical impulses that are sent through electrodes placed over nerve centers. The various pulses employed by TENS can block pain signals normally sent to the brain through nerve fibers, thereby interrupting the brain's awareness of pain. TENS can be used to activate the release of endorphins which are used by the body to suppress pain naturally. TENS car be used for chronic pain (e.g., arthritis or low-back pain) and/or acute pain (e.g., childbirth, traumatic injury or surgery).

A type of electrical therapy used for tissue repair and edema reduction is High Voltage Pulsed Current (HVPC) or High Voltage Pulsed Galvanic (HVPG) therapy which uses a device to provide short duration low amperage high voltage pulses to preselected areas of a patient's tissues through electrical leads or electrodes.

Neuro-Muscular Electrical Stimulation (NMES) uses the same technology as TENS to cause a muscle to "twitch" or contract on purpose. NMES is used for muscular therapy (e.g. for muscle tension, stiffness in joints or back areas, to increase motion from disuse or atrophy or for increasing blood circulation). NMES output current is usually stronger and has a wider pulse width than TENS.

Another type of electrical therapy is Inferential (IF) therapy which differs from TENS and NMES in that it delivers concentrated stimulation deep into the affected tissue. IF therapy exploits the interference of two separately generated sinusoidal currents applied to the body simultaneously.

Interferential stimulators have two standard nodes of operation. The first mode produces two different: output frequencies on two separate output channels that are applied to a patient using four electrodes. The two signals are applied to that patient and allowed to add together at a targeted location on the patient. The second mode takes the same two frequencies, adds them together inside the device and then applies a single channel of stimulation to the patient via two electrodes.

There are clinical devices that perform various types of electrical therapy (such as those described above). However, it is often difficult for a patient to take the time needed to travel to a clinical facility in order to get proper treatment using clinical devices. Portable or handheld devices were developed to overcome the inconvenience required for proper treatment using clinical devices. A typical handheld device performs one type of therapy (e.g., TENS, NMES or IF therapy). Typically, if a patient requires different types of treatment, the patient either has to travel and use a clinical device or purchase multiple portable devices.

Recently, portable devices have been developed which provide more than one type of electrical therapy. For example, there are devices which include both HVPC and NMES electro-therapy (U.S. Pat. No. 5,514,165 issued to Malaugh et al. and U.S. Pat. No. 6,064,911 issued to Wingrove). Though more flexible than single mode devices, these multi-function devices are still limited. For example, multi-function electro-therapy devices do not include IF therapy. Typical handheld IF stimulators create the frequencies through the use of two separate oscillator circuits. One oscillator has a fixed frequency and the other oscillator is controlled by varying either a capacitor's value or a resistor's value in the oscillator circuit. Additional circuitry is used to add the two frequencies together to form the pre-modulated IF waveform. This method of pulse generation generally requires a large number of components and a considerable amount of test and calibration time which increases production costs and decreases reliability. A microprocessor can also be used to either control the two different oscillators or to generate the two required frequencies. To operate in the proper range of frequencies with the proper resolution a very fast and often expensive microprocessor is required. Thus, handheld or portable devices have not used microprocessors to generate frequencies due to prohibitive costs.

Thus, a need exists for a portable electrical therapy device which can perform IF therapy, as well as other types of electro-therapy. In addition, the device should use technology which allows for the device to be produced in a manner which increases reliability without increasing costs.

BRIEF SUMMARY OF THE INVENTION

The present invention is directed to a system and method for performing electro-therapy. The invention is a multi-mode portable electro-therapy device which comprises a microprocessor located in a housing. The microprocessor generates and controls output signals. The device also includes a display, at least one keypad, an electrode jack and at least one pair of electrodes connected to the electro-therapy device via the electrode jack. Output signals are transmitted to a patient via the electrodes.

In accordance with other aspects of the invention, the multiple modes of the device comprise an interferential mode, a pre-modulated interferential mode, a neuromuscular mode and a high volt pulse current mode. The output signal may be generated by combining two signals, for example when in interferential mode. The two signals may be started at different times.

In accordance with still other aspects of the invention, the output current may be a constant output voltage or a variable load. The output current may be monitored. R variable load current may be adjusted based on the monitored output. The monitored output may be stored. The stored monitored output may be used for later evaluation, for example to determine skin resistance. The output signal can be modified based on a change in voltage. For example, as battery power decreases, the output signal can be modified so that the output signal remains constant.

In accordance with yet other aspects of the invention, new modes can be created by combining existing modes. For example, one mode may automatically follow another mode.

In accordance with further aspects of the invention, the output signal comprises a duty cycle. The output signal can be varied by changing the duty cycle.

In accordance with yet other aspects of the invention, available functions are based on the user. For example, a patient can modify the amplitude of a signal being output. However, a medical professional, such as a doctor, can perform functions, such as defining modes, which cannot be performed by a patient.

In accordance with still other aspects of the invention, a calibration device may be connected to the electro-therapy device via the electrode jack. An external device, such as a computer, may also be connected to the electro-therapy device via the electrode jack. Data is transmitted to the external device via the electrode jack for processing. For example, stored monitored data can be viewed and/or analyzed.

In accordance with other aspects of the invention, output signals are generated using a microprocessor (i.e., the signals are generated using software). The method employed by the electro-therapy device performs the following steps: (1) accepts inputs for defining at least one mode of therapy; (2) determines the mode of electro-therapy; (3) uses a microprocessor to calculate at least one output signal based on the mode of therapy; (4) transmits the at least one output signal to at least one pair of electrodes; and (5) monitors for a change in mode. The above steps (3–5) are repeated until the transmission of the output signal is terminated (e.g., end of therapy, device turned off).

In accordance with still other aspects of the invention, the electro-therapy device may be calibrated. For example, calibration may occur when the device is turned on. Preferably, additional calibration functions can be performed upon request.

In accordance with yet other aspects of the invention, output may be monitored and stored. Signals may be adjusted based on the monitored output.

BRIEF DESCRIPTION OF THE DRAWINGS

These as well as other features of the present invention will become more apparent upon reference to the drawings wherein:

FIG. 4 is a block diagram illustrating exemplary components for forming an electro-therapy device in accordance with the present invention;

DETAILED DESCRIPTION OF THE INVENTION

Figures 1, 2:
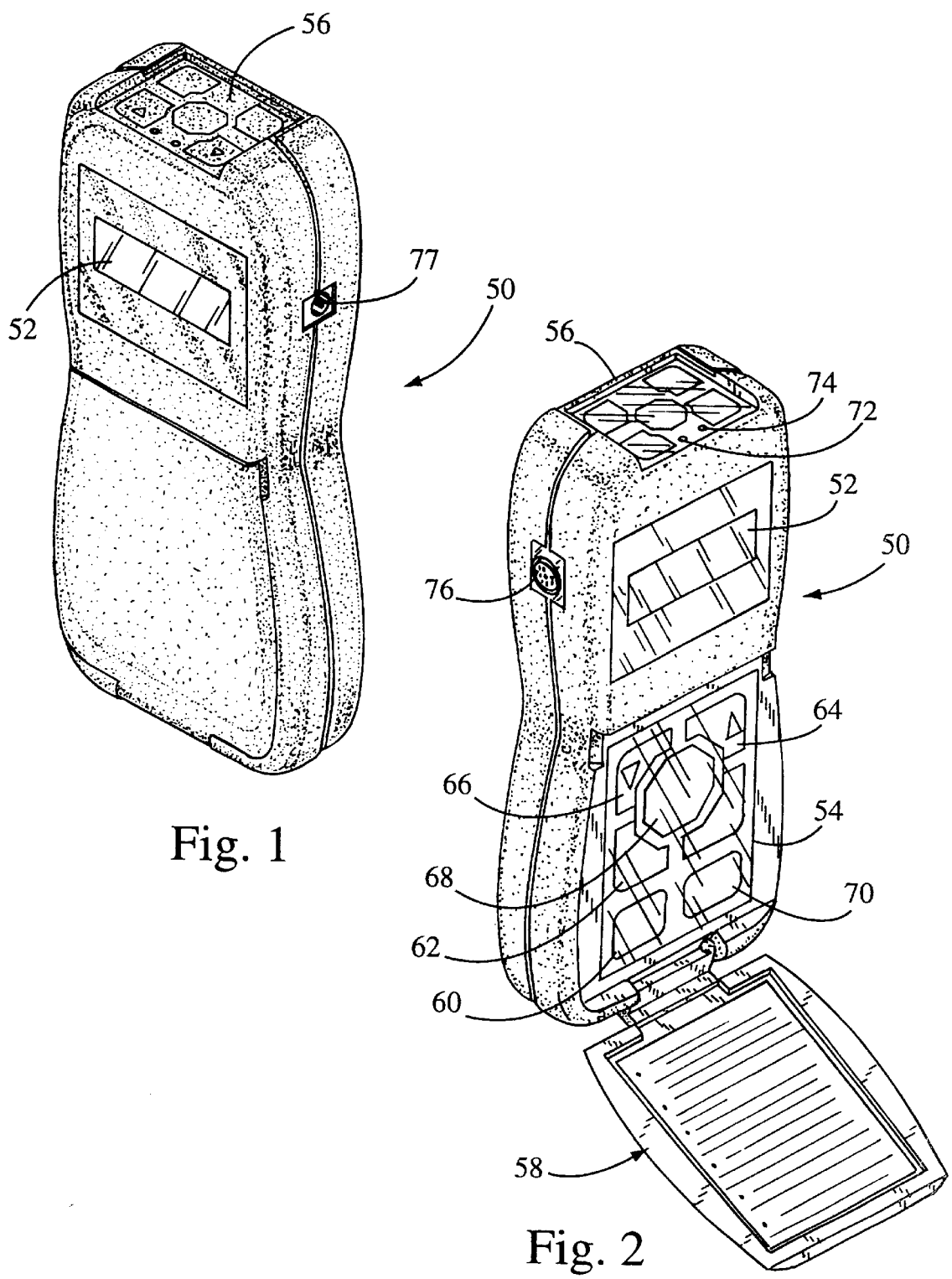
FIG. 1 is a front right perspective view of a multi-function electro-therapy device formed in accordance with the present invention.
FIG. 2 is a front left view of the electro-therapy device shown in FIG. 1 with the door opened to reveal a user keypad.

The present invention shown in FIGS. 1 and 2 is a portable multi-mode electrical stimulator 50 which uses software (a microprocessor) to generate and control output signals. In exemplary embodiments, the present invention is a two-channel IF/NMES/HVPC stimulator with selectable modes of stimulation with parameters that can be individually controlled using a control panel and display 52 which are located on the exterior of the device housing. As can be seen in FIG. 2, exemplary embodiments include a front control panel 54 which can be accessed by opening a cover 58 and an upper control panel 56.

Figure 3:
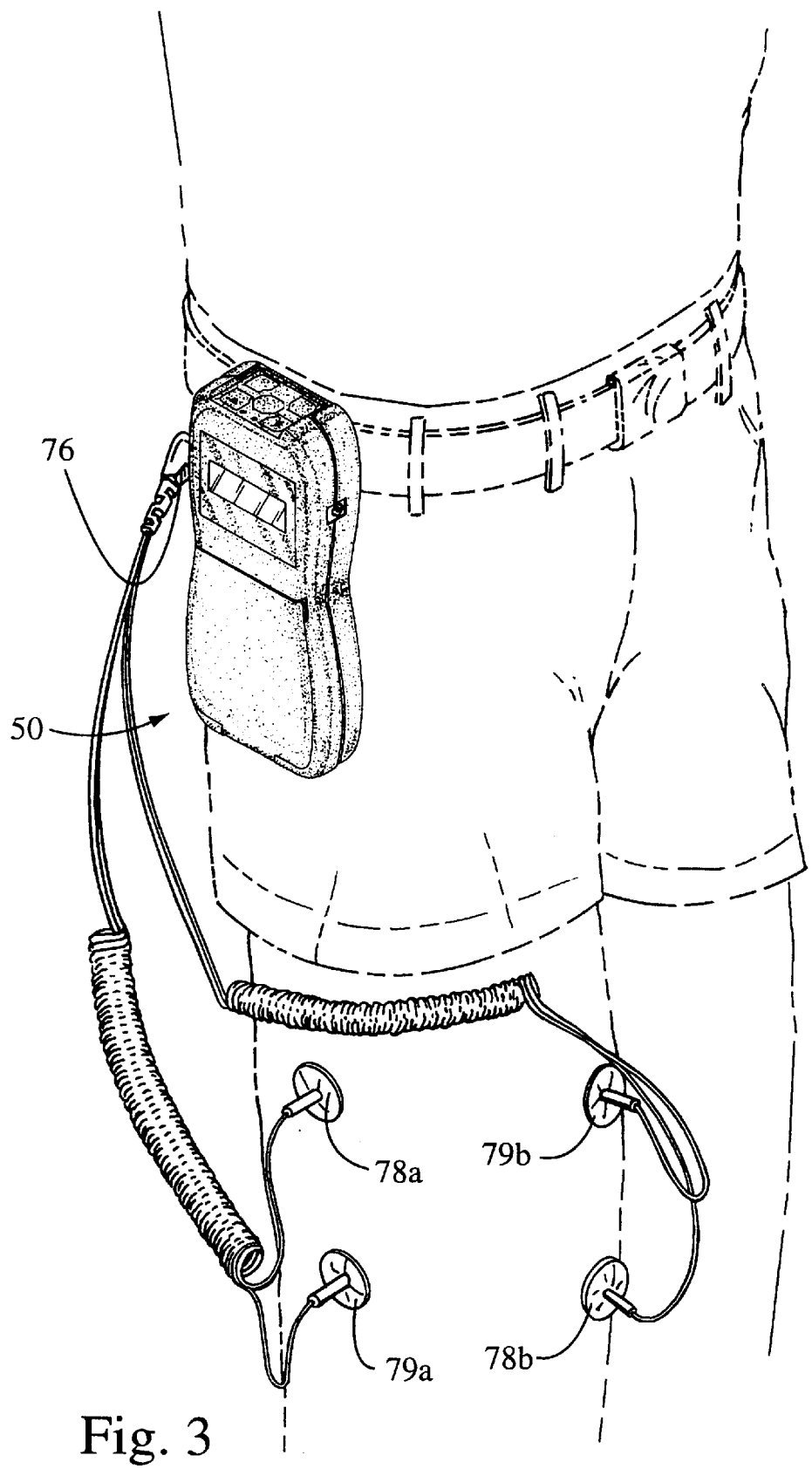
FIG. 3 illustrates the electro-therapy device of FIG. 1 being used by a patient.

The front control panel 54 can be used to operate the present invention when the electro-therapy device 50 is placed on a table top or similar surface. The electro-therapy device 50 can be worn on a belt as shown in FIG. 3. Preferably, a belt clip (not shown) is attached to the back of the device 50. The device 50 can be operated using the upper control panel 56 when the device is worn on a belt as shown in FIG. 3.

In exemplary embodiments, the control panels 54 and 56 have an On/Off button 60, a Preset button 62, an Increase button 64, a Decrease button 66, a Pause button 68 and a Display button 70. The On/Off button is depressed in order to turn on the electro-therapy device 50 to start therapy. When the device is turned on, it starts with an intensity of zero. Once the device is turned on, the On/Off button 60 can be pressed at any time to stop therapy and turn off the device 50. The Preset button 62 allows the user to select from preset (stored) treatment protocols. The Increase button 64 and Decrease button 66 are used to increase and decrease the intensity of the stimulation, respectively. The level of stimulation is shown on the display 52. The Pause button 68 stops stimulation but leaves the electro-therapy device 50 on. Pressing the Pause button 68 again resumes the therapy at the same point in the therapy program. The Display button 70 allows the user to cycle through the available display options. In exemplary embodiments, the displays include an Intensity display, a Remaining Time display and an Elapsed Time display. Exemplary user interface displays are shown in FIGS. 24A–24G and described later.

Exemplary embodiments may include indicator lights, for example an On indicator 72 and a Battery indicator 74. The On indicator 72 is lit when the electro-therapy device 50 is on and operating. The Battery indicator 74 flashes when batteries are nearly depleted (e.g., from 15 minutes to two hours remaining). In exemplary embodiments, indicator lights are located on the top of the device along with upper control panel 56.

Exemplary embodiments include a lead wire socket 76. An electrode lead wire is plugged into the lead wire socket 76. Preferably, the same lead wire is used for all types of stimulation provided by the device 50. In the exemplary embodiment shown in FIG. 3, there are two pairs of electrodes (4 electrodes) attached to the lead wire. Preferably, the electrodes are reusable, self-adhering electrodes which can be applied to the patient's skin area. The electrode lead wire may be replaced by another lead wire and connected to a computer in order to perform calibration on the electro-therapy device 50 or to download data stored in the electro-therapy device to a computer for analysis.

FIG. 4 is an exemplary block diagram illustrating various components and their interfaces for forming an electro-therapy device in accordance with the present invention. As described above, there is at least one control panel or keypad 84. User inputs from the keypad 84 are read and interpreted by a microprocessor or micro controller 80. The micro controller retrieves data (e.g., stored modes) from memory 82. The micro controller 80 also stores data (e.g., updated modes, patient monitoring data) to memory 82.

The micro controller 80 performs calculations based on information retrieved from memory 82 (e.g., the mode), from the keypad 84 (user adjustments, such as increasing or decreasing amplitude) and monitored output (e.g., patient's reaction to output) to determine the signal to be output to the patient. In the exemplary embodiment illustrated in FIG. 4, depending on the mode, the micro controller 80 outputs data to an appropriate output circuit (e.g., IF/NM output circuit 92 or HV output circuit 94). The output circuit 92 or 94 forwards information to output switching module 96 which outputs the appropriate signal to the patient via electrodes.

Information (e.g., mode and parameters, elapsed time, remaining time) is displayed to the user via a display 86. Information may also be provided to the user via indicator lights (e.g, LEDs) 88. The portable electro-therapy device 50 includes a power supply 90 which is powered by batteries 91. Exemplary embodiments can be also be run using electricity if desired. An AC adapter may be plugged into an AC jack (77 of FIG. 1).

Figure 5A:
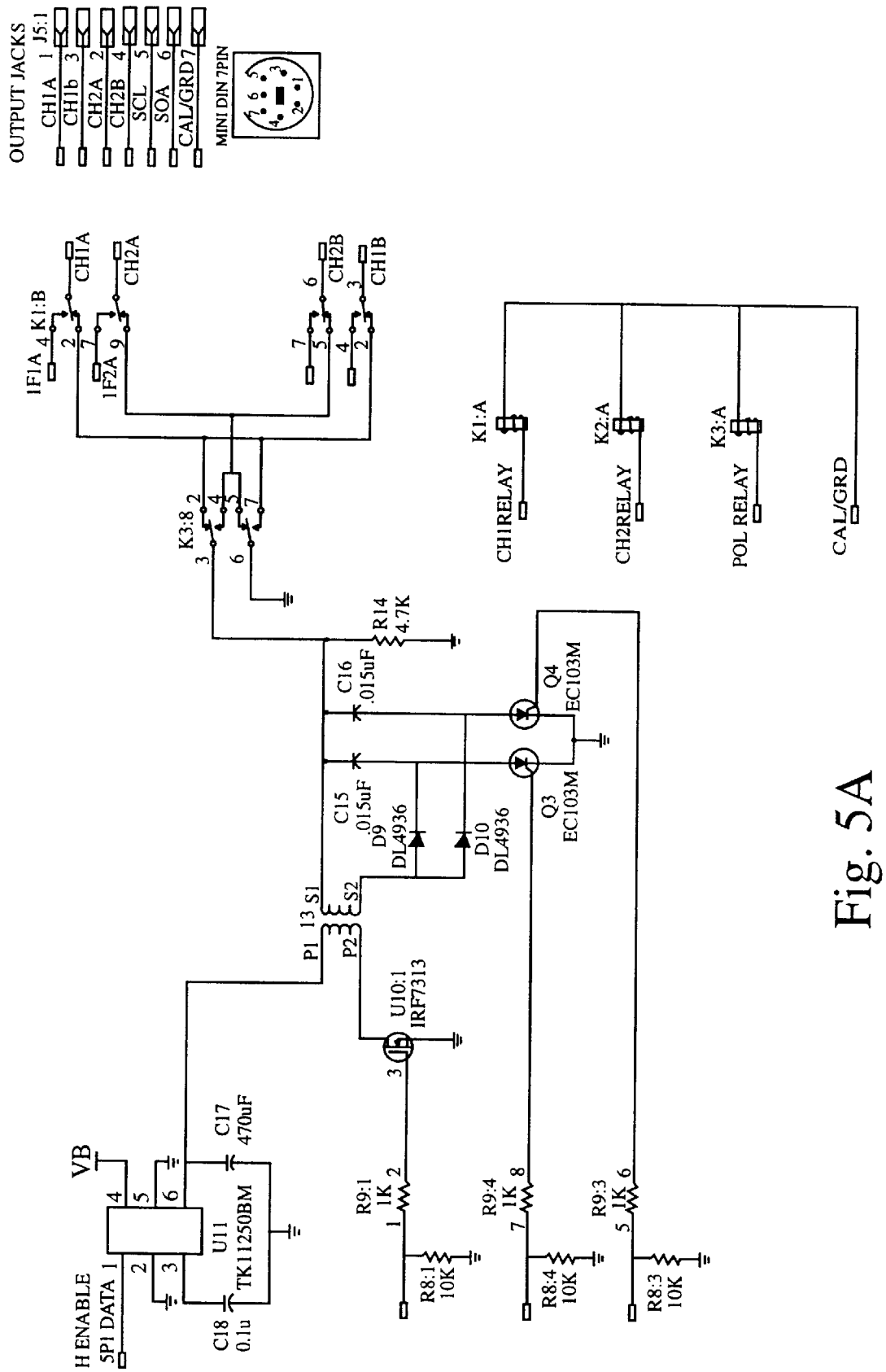
FIGS. 5A–5E are an electrical schematic of a multi-function electro-therapy device formed in accordance with the present invention.
Figure 5B:
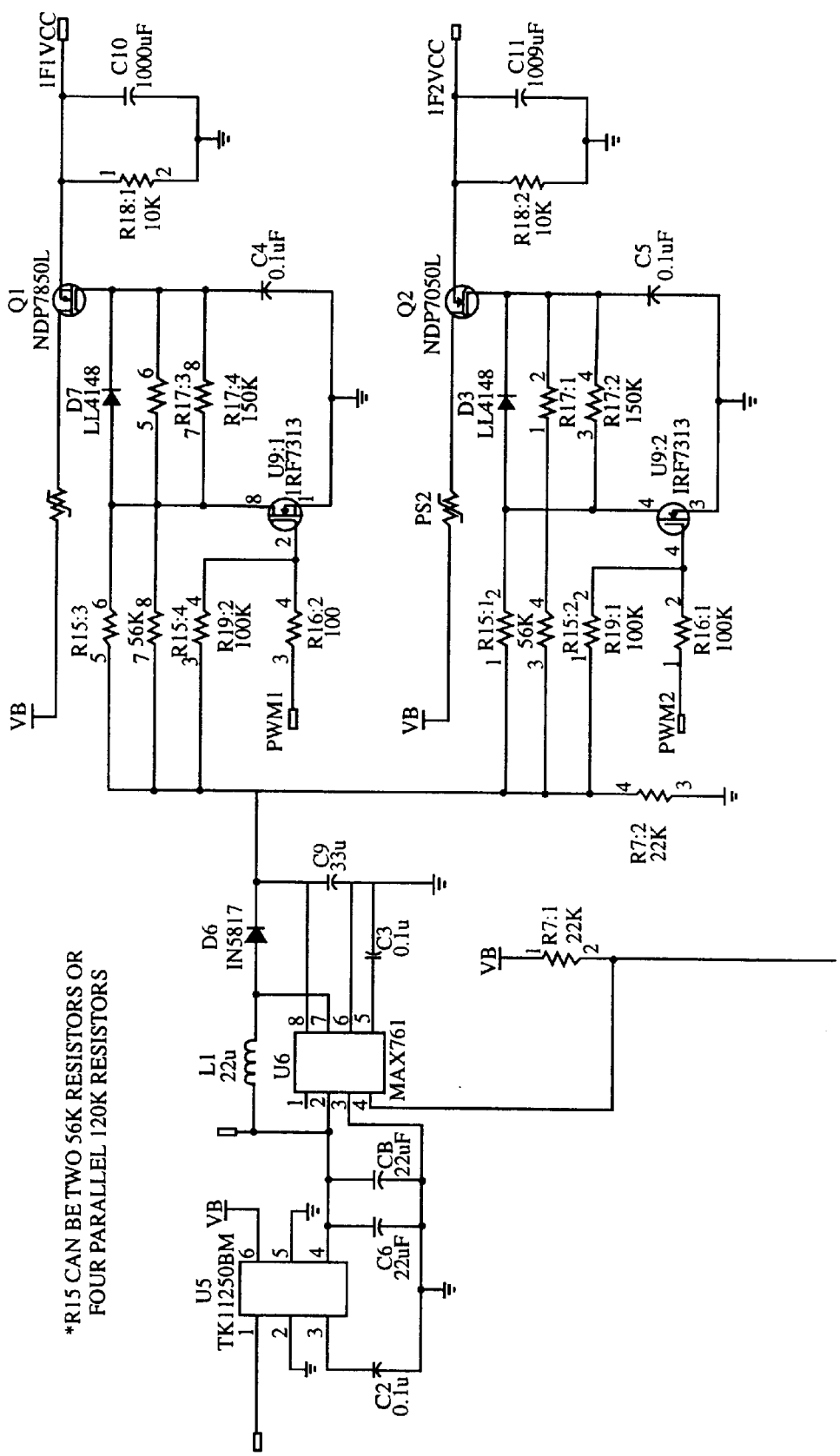
Figure 5C:
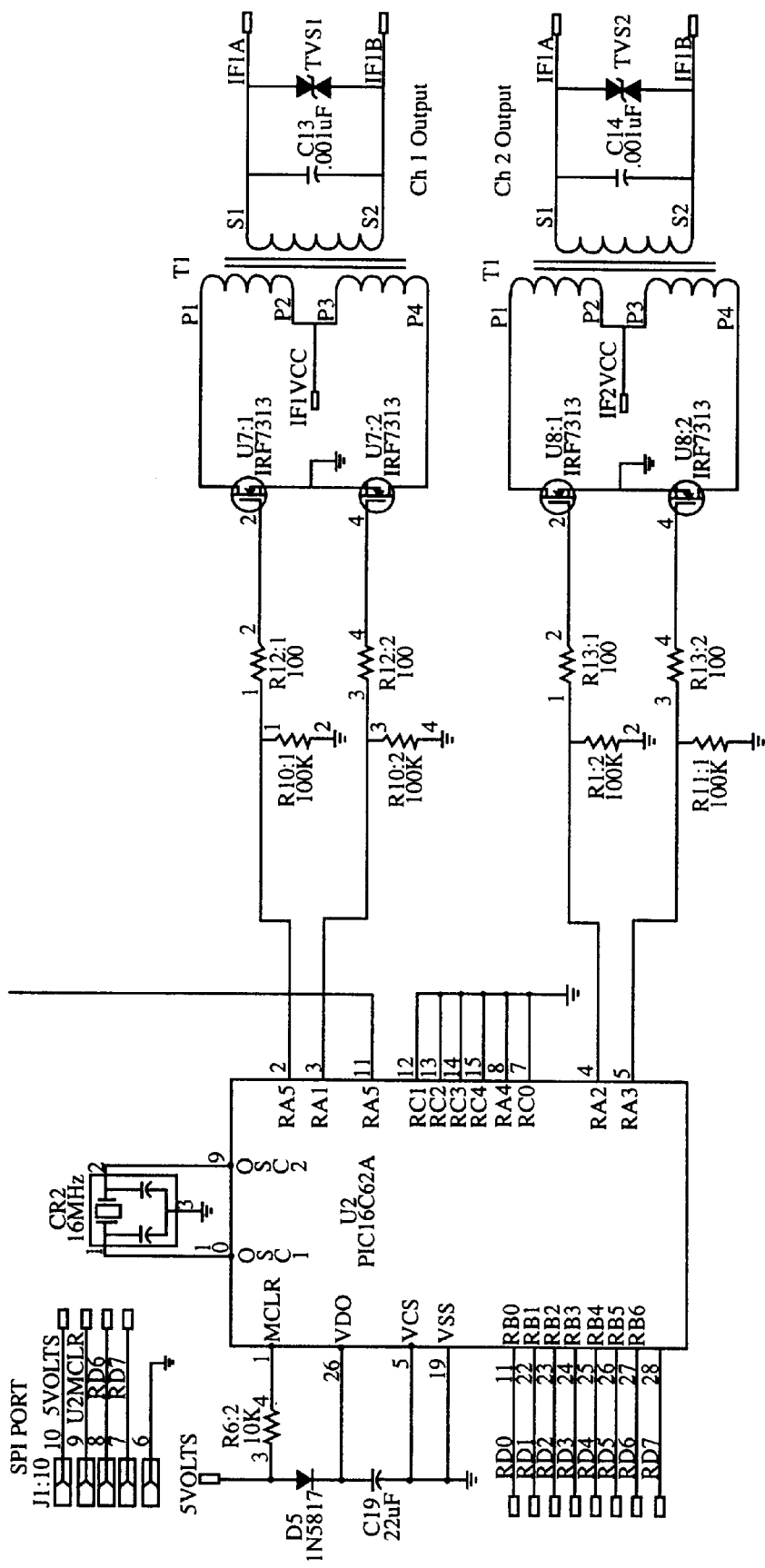
Figure 5D:
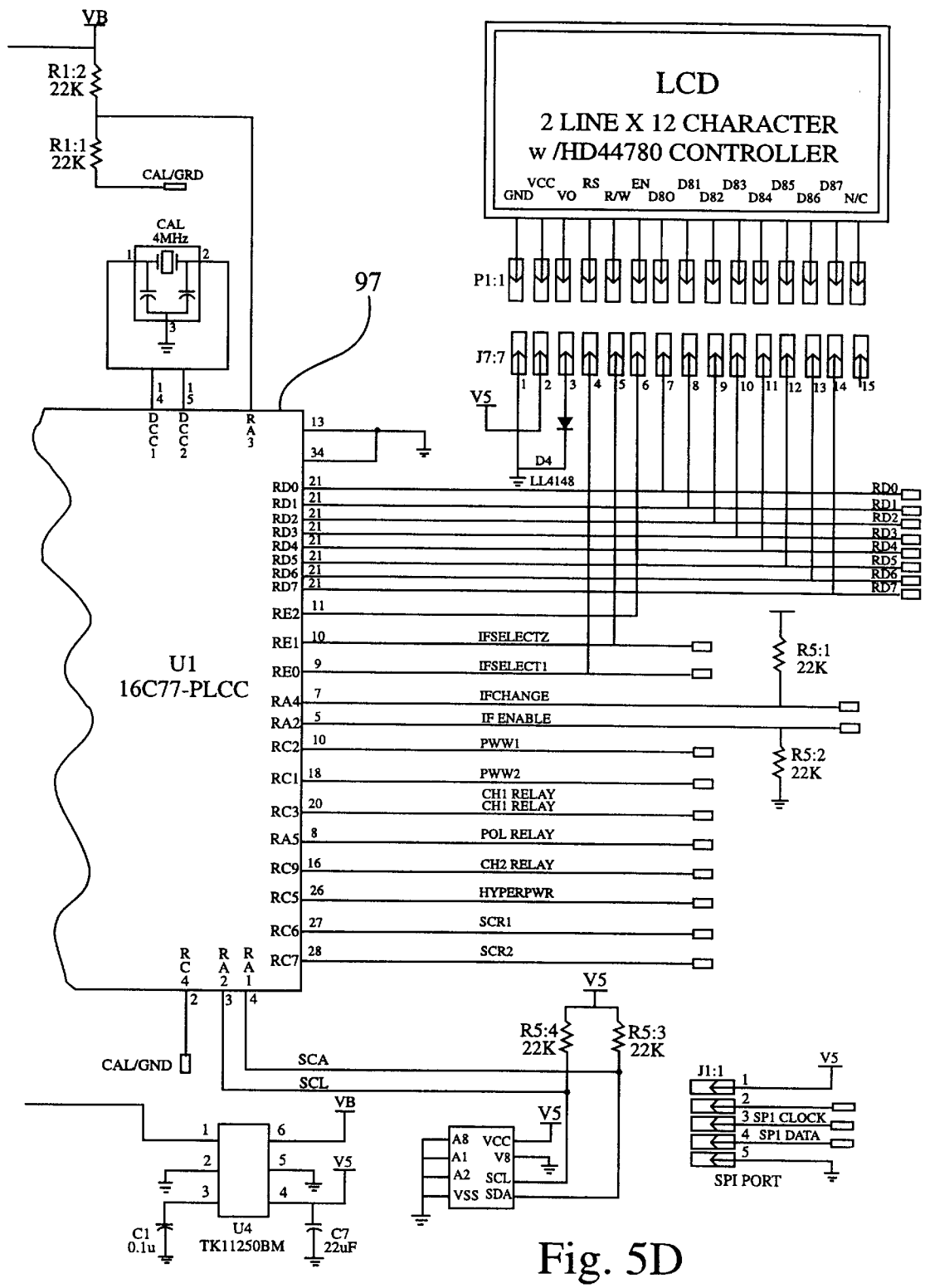
Figure 5E:
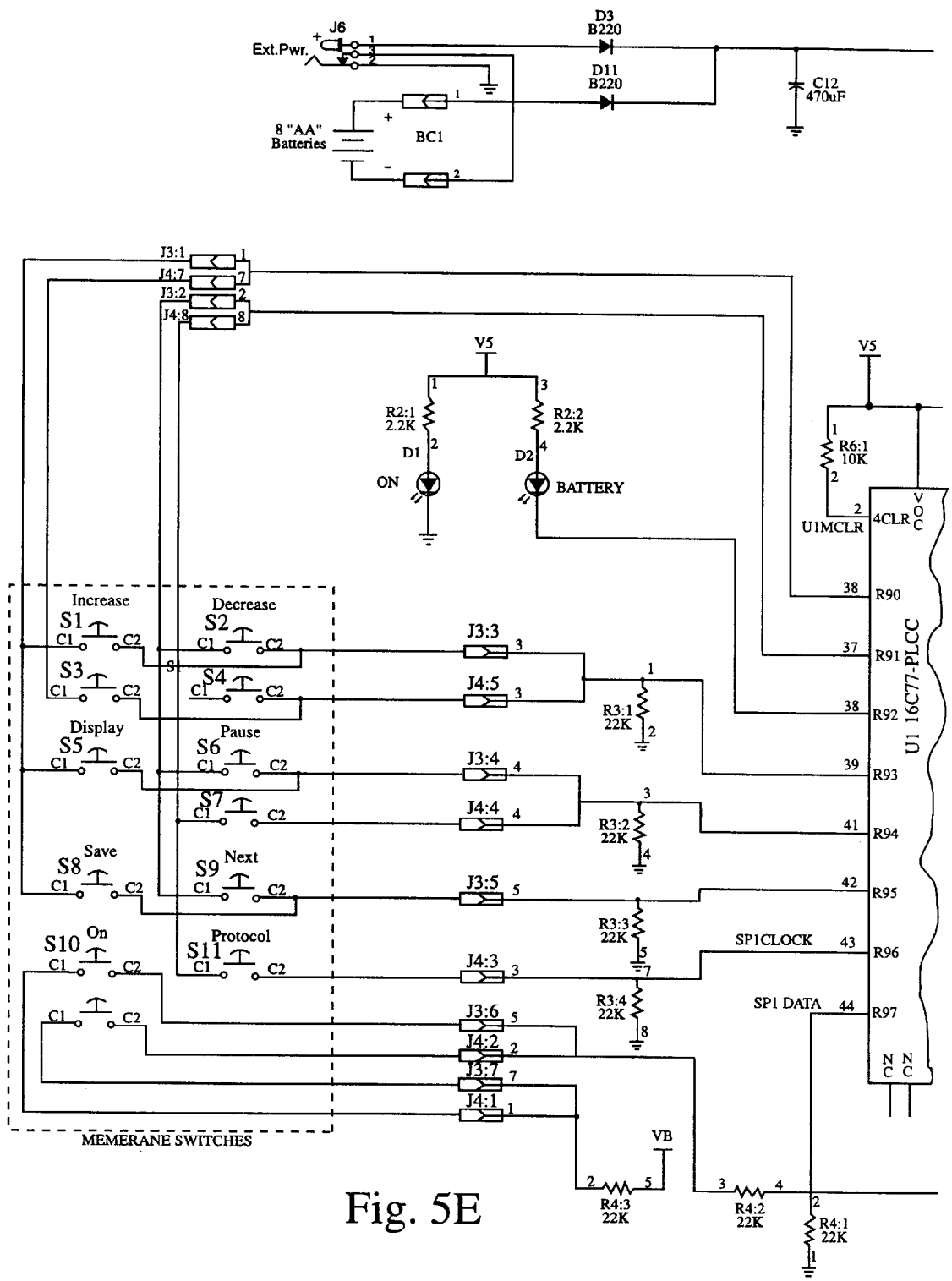

As described above, the processing of the present device is performed using a micro-controller 80. Prior art electro-therapy devices also include a micro-processor (e.g., for storing various modes and parameters). However, the present invention, unlike prior art devices, also uses a micro controller for generating output signals. FIGS. 5A–5C illustrate an electrical schematic suitable for implementing the present invention. The electrical components are contained within the housing of the portable electro-therapy device 50 of the present invention. Those of ordinary skill in the art will appreciate that the components shown in FIGS. 5A–5C are the same as those found in typical portable electro-therapy devices. However, since the waveforms of the present invention are generated in software rather than hardware, there are substantially fewer components (e.g., capacitors, coils, resistors) in the present invention than in prior art portable electro-therapy devices. The embodiment shown in FIGS. 5A–5C includes two micro-processors. The first microprocessor (97 of FIG. 5C) performs substantially the same functionality as that performed by prior art electro-therapy devices. The additional micro-processor (98 of FIG. 5B) generates the output signals and essentially replaces the hardware components used to generate output signals that are in prior art devices but not in the present invention. It will be appreciated that other configurations are possible, for example, all functionality could be preformed on a single microprocessor, the functionality could be distributed differently (e.g., each of the two microprocessors performing some of the output signal generation, or there could be more than one microprocessor generating the output signals (e.g., three microprocessors).

In exemplary embodiments of the present invention, anyone using the device (e.g., a patient, a doctor, or a manufacturer) can turn the device on and off, select one of the stored modes, and adjust the amplitude (strength) of the signal being output using keys on either one of the control panels 54 and 56. Medical personnel (e.g., physicians) are provided with an access code which allows additional functionality, such as defining new modes and modifying stored modes. In exemplary embodiments, the access code is defined by a specific sequence of depressing buttons which may include pressing multiple buttons simultaneously and/ or pressing a button several times in succession and/or pressing one or more buttons for an extended period of time. In exemplary embodiments, the manufacturer also has an access code which allows the manufacturer to perform calibration functions.

In exemplary embodiments, as the device is being used, the output is monitored and stored. The physician can view the stored output. The information stored includes data such as when the device was used, and for how long, as well as amplitude changes made by the user. By examining the stored output, a doctor can determine prior use and effect in order to adjust the stored protocols if necessary. Since people are different (e.g., have different skin resistance), therapy may need to be adjusted based on the individual. For example, a doctor may initially set protocols based on an average user. However, it may later be discovered that the patient's skin resistance is above average, thus requiring the amplitude to be increased. According to Ohm's law:

$$\text{Voltage} = \text{Current} * \text{Resistance} \tag{1}$$

Figure 6:
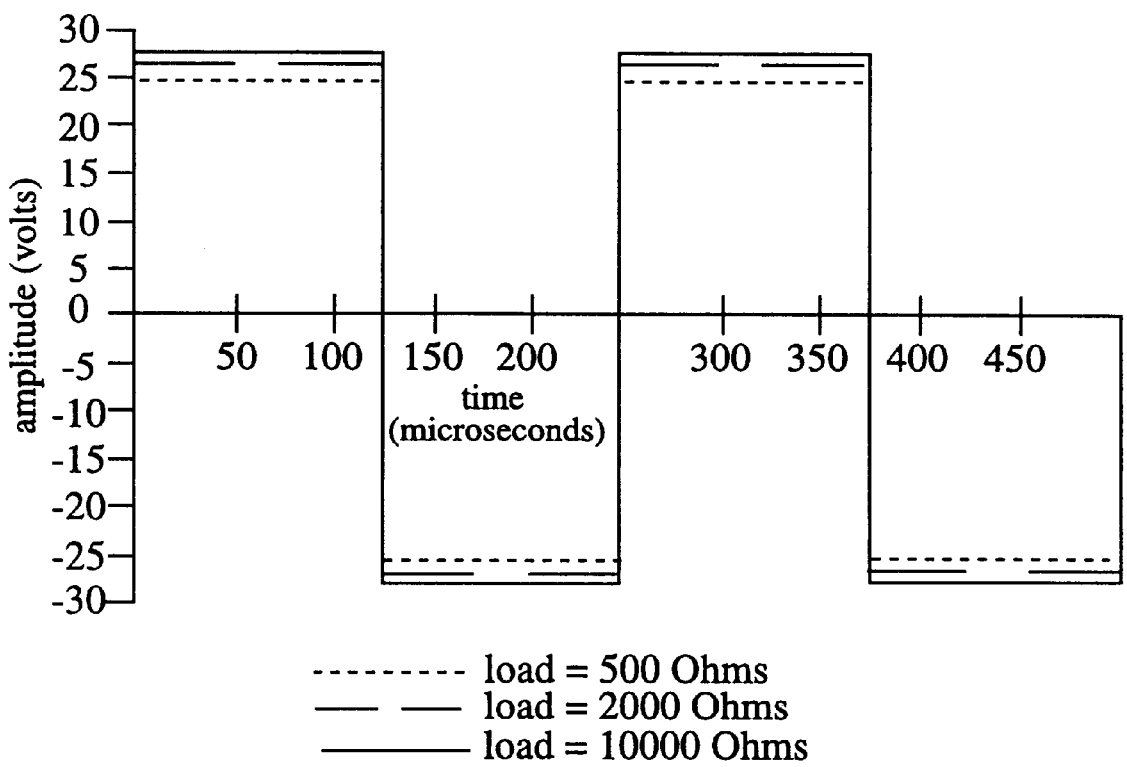
FIG. 6 illustrates exemplary waveforms with restrictive loads for IF therapy.
Figure 7:
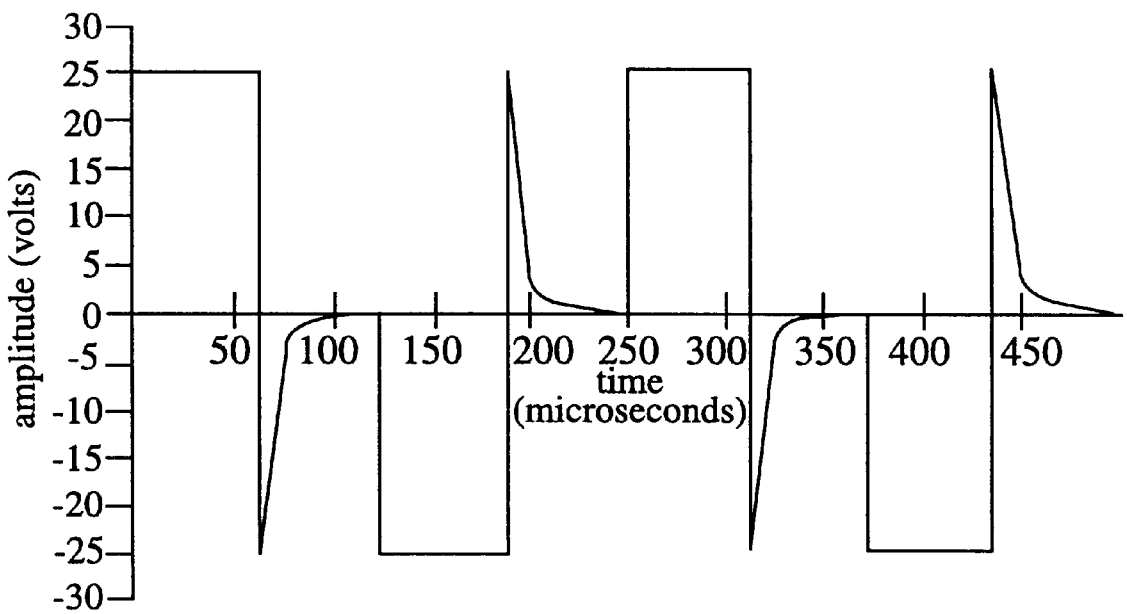
FIG. 7 illustrates exemplary waveforms with restrictive loads for pre-modulated IF therapy.
Figure 8:
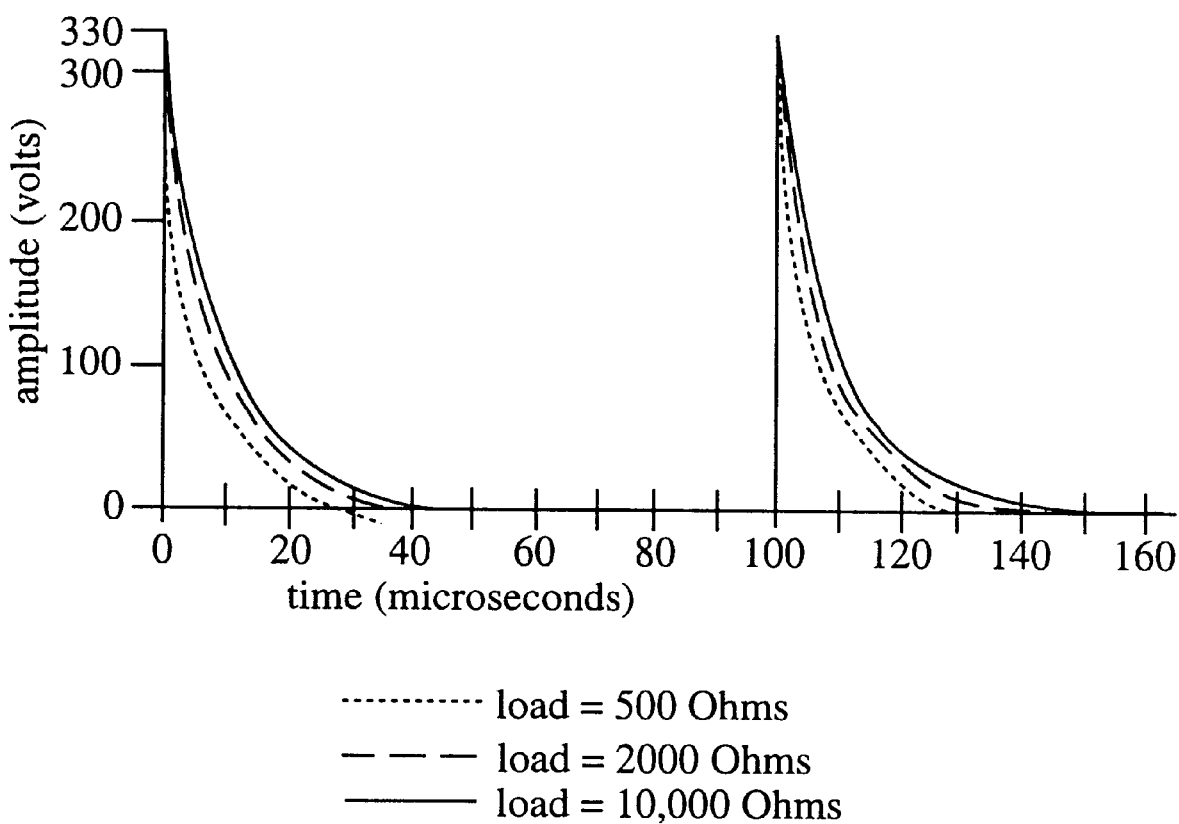
FIG. 8 illustrates exemplary waveforms with restrictive loads for HVPC therapy.

In exemplary embodiments, output voltage may be constant or based on a variable load. Preferably, in defining a mode or protocol, a physician can specify whether the voltage is constant or based on a variable load. If voltage is constant, then the selected amplitude (voltage) is not automatically adjusted. FIG. 6 illustrates an output waveform with resistive loads (500 Ohms, 2000 Ohms and 10000 Ohms) using standard (4-electrode) IF. For example, if a patient selects an amplitude of 25, a waveform is output to give 25V. Referring to FIG. 6, 500 Ohms should produce the desired output of 25V. However, based on the patient's skin resistance, the monitored output may not be 25 V. Thus, the amplitude may have to be adjusted accordingly. If the mode is a variable load mode, the electro-therapy device 80 of the present invention will automatically adjust the amplitude in order to obtain the desired output. However, if the voltage is constant, the output will remain at 500 Ohm (the amount required to output 25V assuming normal skin resistance) even though the monitored output is not 25 V. FIG. 7 illustrates the output waveform for pre-modulated (2 electrode) IF with a 500 Ohm resistive load. FIG. 8 illustrates exemplary HVPC output waveforms with resistive loads of 500 Ohms, 2000 Ohms and 10000 Ohms.

Figure 9:
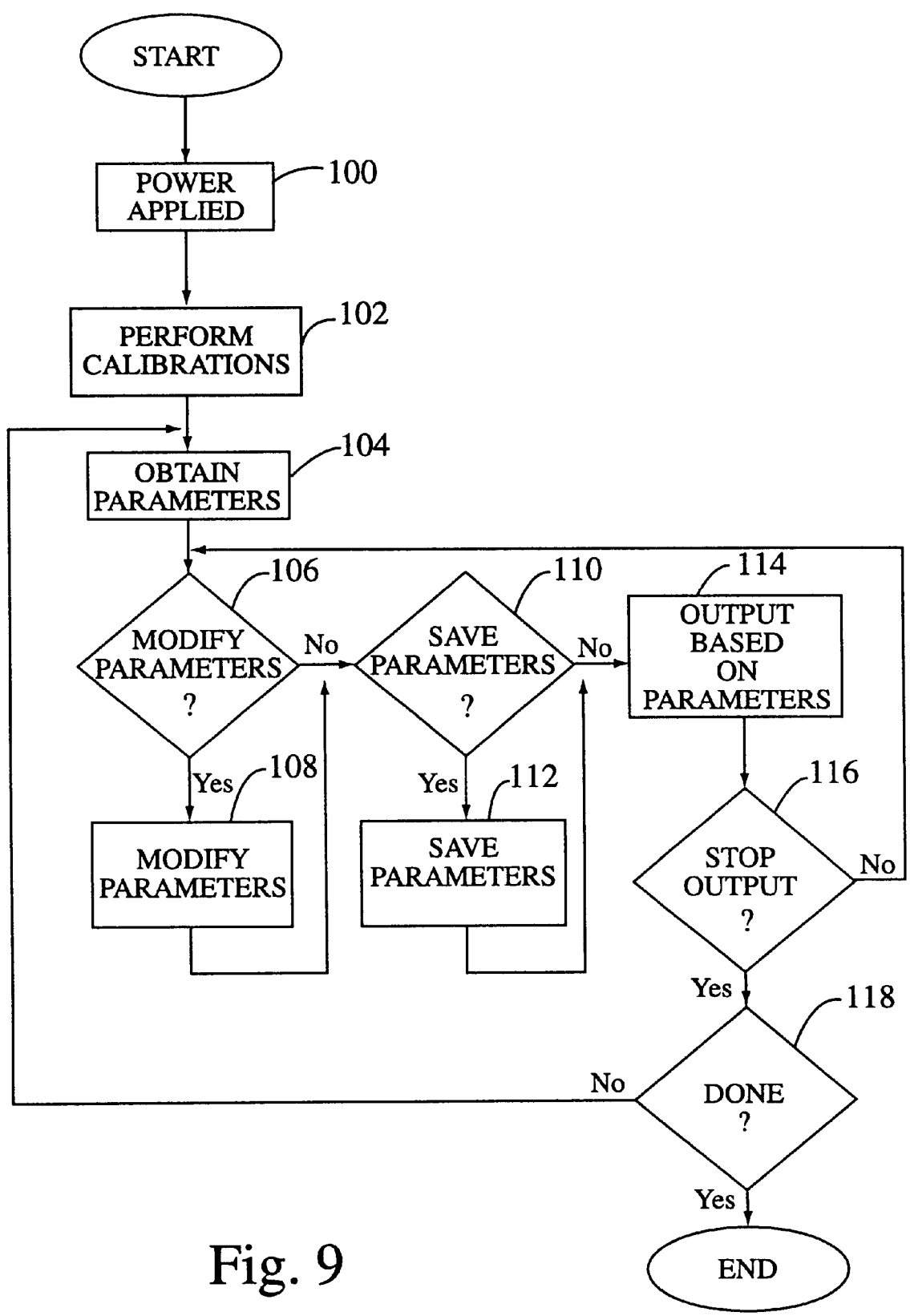
FIG. 9 is a flow diagram illustrating exemplary logic performed by a microprocessor of the electro-therapy device shown in FIG. 1.

FIG. 9 is a flow diagram illustrating exemplary logic performed by the microprocessor of the present invention. The logic moves from a start block to block 100 where power is applied. In exemplary embodiments, there is an ON/OFF button on keypads 54 and 56. In exemplary embodiments, when power is applied, a calibration function is performed (block 102). Once calibration has been applied, a determination of what to do is determined by obtaining parameters (block 104). Preferably, the initial display will display the first pre-defined mode with an amplitude of zero. Thus, the user must either select a new mode and/or increase the amplitude in order to begin the therapy. Preferably, at any time (during any mode of operation), the user can stop the therapy (for example, by turning the machine off or setting the amplitude to zero).

Once the parameters (e.g., settings for current mode) have been obtained, a determination is made as to the flow of the logic. Parameters may be modified at any time. As described above, various users (e.g., patient, doctor) may have different levels of access. If a parameter is modified (yes in decision block 106), the logic moves to block 108 where the parameter is modified. For example, the patient may adjust the amplitude or the doctor may modify a mode or add a new mode. If parameters are to be saved (yes in decision block 110), the logic moves to block 112 where the parameters are saved, for example, a new or modified mode stored by a doctor or output parameters based on monitored output. The logic continually monitors for changing parameters and parameters or other data that should be saved.

Additionally, the logic continually tracks what signal, if any, should be output via the electrodes. The signal to be output is based on the mode and the parameters for the current mode. Exemplary modes are described in further detail below. If it is determined in decision block 106 that output should be terminated (e.g., amplitude is zero or off key is depressed), the logic moves to block 118 to determine if processing is done (e.g., off key is depressed). If processing is done, the logic of FIG. 9 ends. If processing is not done, the logic returns to block 104, and processing continues as described above. It will be appreciated that certain modes of therapy output a signal (block 114), wait a specified period of time and the output another signal, etc. or that there may be a period of time that no signal is output when transitioning from one mode to another. In such cases, output is stopped (even though it may only be for a brief period of time), but processing is not done (yes in decision block 116 and no in decision block 118). In these cases, the logic returns to block 104 and processing continues. The next signal is output (block 114) at the appropriate period of time based on the current mode and parameters.

As mentioned above, the electrical stimulator of the present invention can operate in multiple modes. An exemplary embodiment operates in the following modes: (1) Interferential (IF) mode (uses four electrodes); (2) pre-modulated IF mode (uses (2 electrodes); (3) Neuromuscular (NM) mode (gated IF or gated pre-modulated IF); and (4) High Voltage Pulsed Current (HVPC) mode. It will be appreciated that various embodiments can include different or additional modes, for example, a device may also include TENS and NMES. In exemplary embodiments of the invention protocols can be created by defining a therapy which consists of multiple types (modes) of therapy, for example, IF stimulation can automatically be followed by HVPC stimulation. Many different protocols can be selected and saved in the internal memory.

Figure 10:
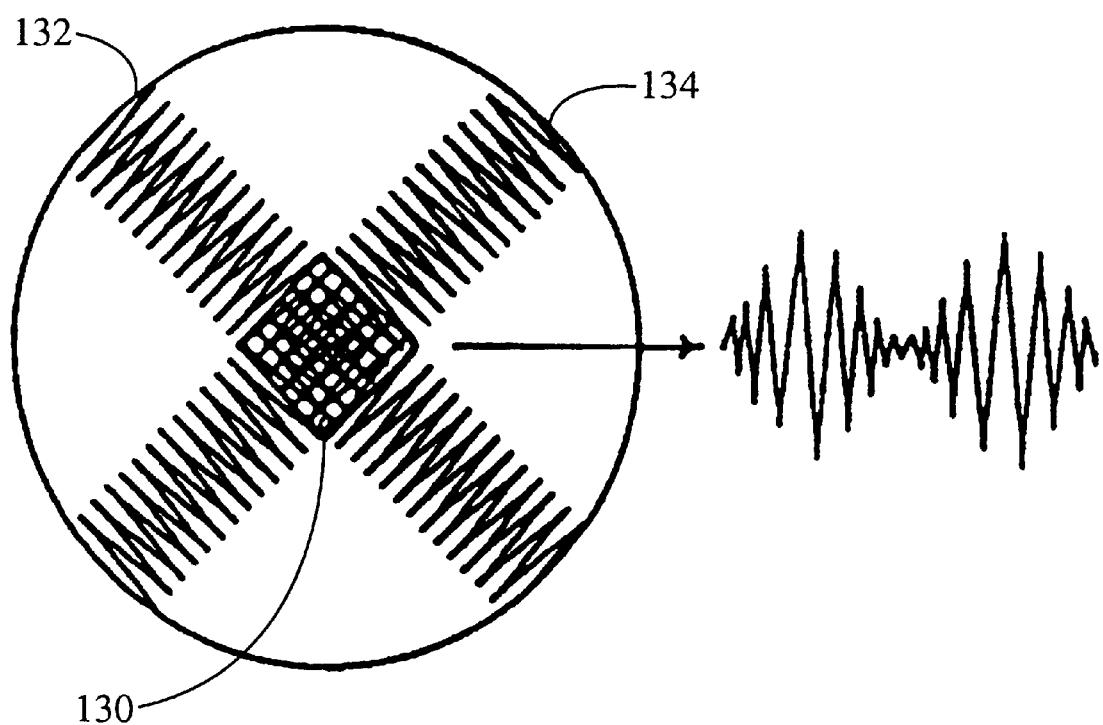
FIG. 10 is a conceptual illustration showing 4-electrode IF stimulation.
Figure 11:
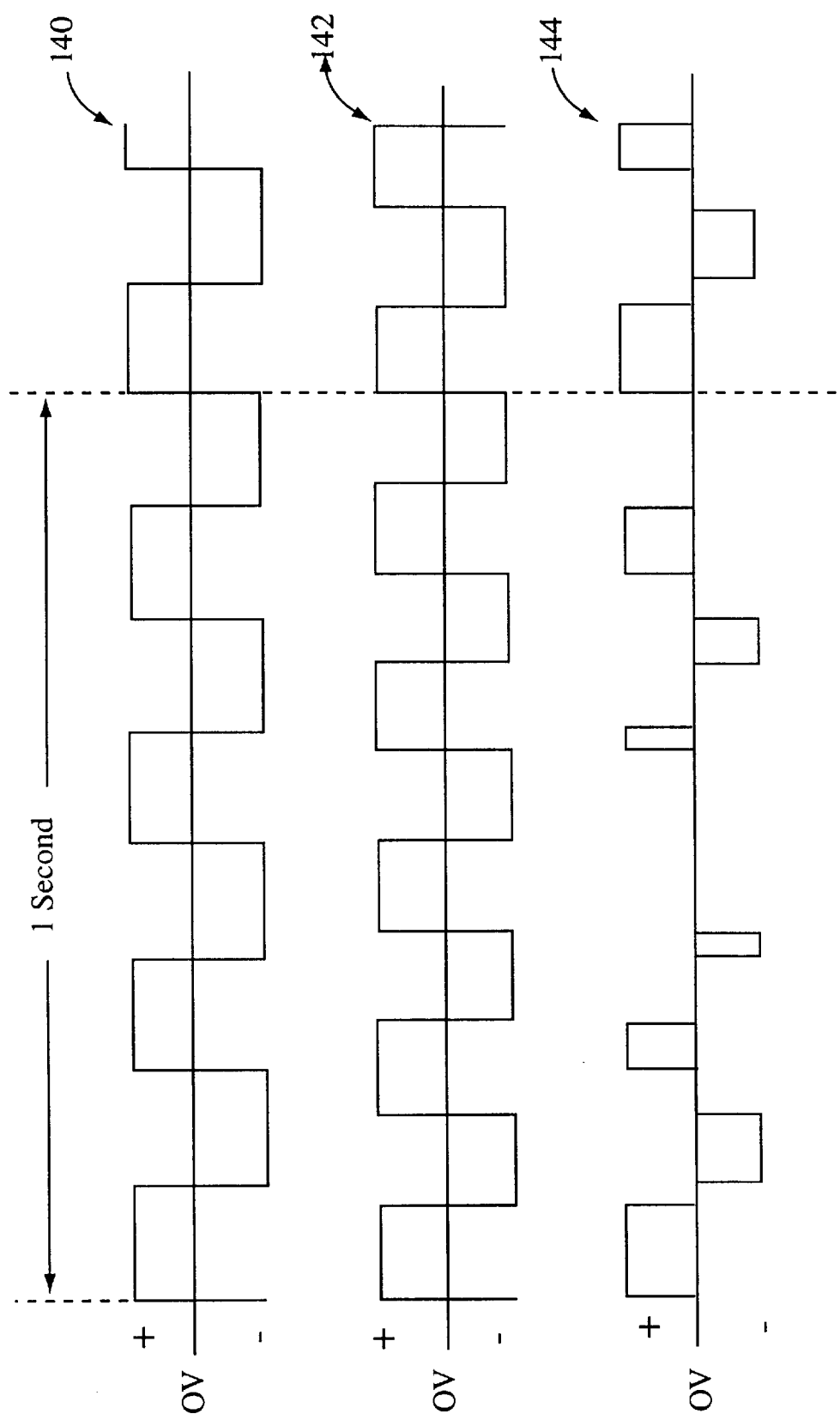
FIG. 11 is a simplified example illustrating adding two waveforms.
Figure 12:
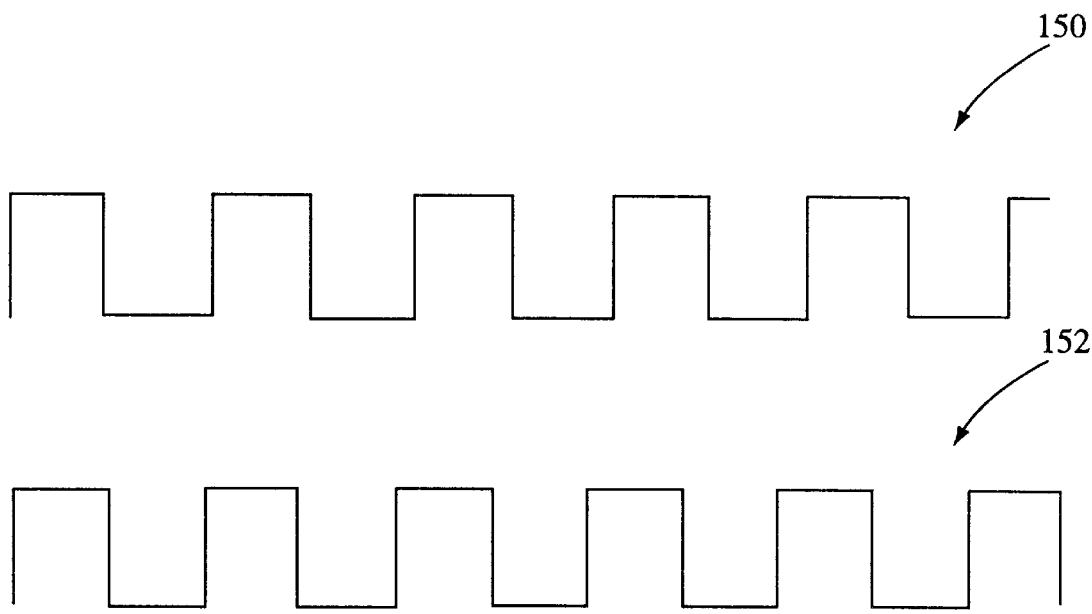
FIG. 12 is an exemplary illustration of generating two waveforms with hardware (e.g., capacitors.
Figure 13:
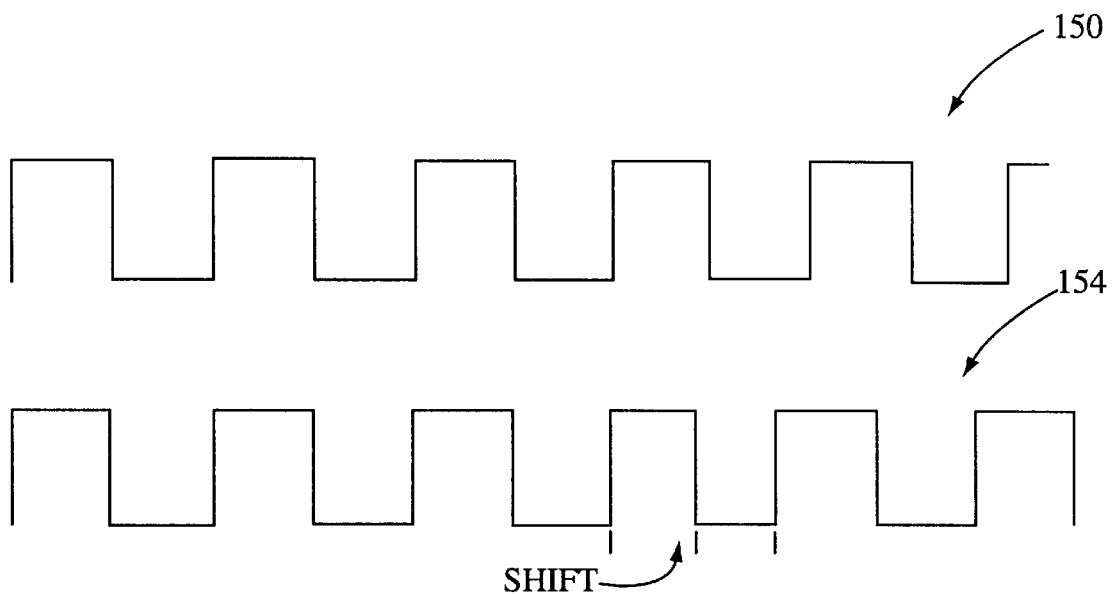
FIG. 13 illustrates using a shift at periodic intervals in order to produce signals in software similar to the hardware signals used to produce the waveforms shown in FIG. 8.
Figure 14:
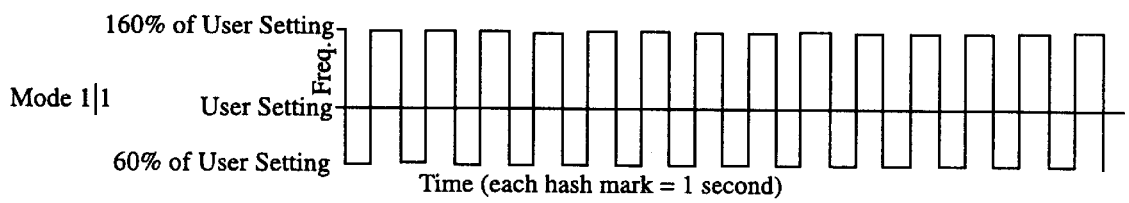
FIG. 14 illustrates an exemplary 1|1 pulse coordination waveform when the electro-therapy device of the present invention is operating in IF mode.

As described above, IF therapy exploits the interference 130 of two separately generated sinusoidal currents 132 and 134 applied to the body simultaneously as shown in FIG. 10. FIG. 10 is a conceptual diagram illustrating quadripolar (4-electrode) stimulation with interference taking place within the tissue from IF therapy with an electrode placement such as that shown in FIG. 3. FIG. 11 and the description below provide a simplistic (non-realistic) example illustrating adding signals together, while FIGS. 12–14 provide a realistic example illustrating IF waveforms.

FIG. 11 is a simple example illustrating a 4 Hz (4 pulses per second) waveform 140 and a 5 Hz waveform 142. When the waveforms are added together, a third waveform 144 results. This third waveform 144 is the signal which results in the electro-therapy treatment received by the patient. In the example shown in FIG. 11, the two waveforms 140 and 142 start off together and after one second start together again. The time for one pulse at 4 Hz is ¼ or 0.25 seconds. The time for one pulse at 5 Hz is ⅕ or 0.2 seconds. The resolution required to generate these signals with one processor is the difference between the two waveforms 140 and 142 which in the example above is 0.25 seconds–0.2 seconds or 0.05 seconds.

If electro-therapy devices could operate at cycles of 4 Hz or 5 Hz, inexpensive microprocessors which are available today (and used in portable electro-therapy devices) could be used. However, electro-therapy devices do not operate in cycles of 4 Hz or 5 Hz. The exemplary electro-therapy device of the present invention operates in the 4000 Hz range.

The present invention generates the desired stimulation waveforms as described next. A fixed frequency is generated by a microprocessor (98 of FIG. 5B). A second frequency is generated at the same time and at predetermined times is shifted by a predetermined amount so that the two frequencies shift in and out of phase. The determination of the proper number of shifts and the required shift amount to make in each given cycle can be made based on the speed of the microprocessor and rate of change of charge desired. A very large shift can be felt by the patient, whereas a very small shift would require a very high speed microprocessor. A middle point is used that does not compromise patient sensation and does not require a very high speed microprocessor. Since the two identical frequencies are added, the duty cycle will vary from 0% to 100%.

When the present invention is operating in the IF mode with four electrodes, there are two channels, with the first channel generating a 4000 Hz square wave 150 of FIG. 12 and a second channel generating a 4000 Hz plus beat frequency 152. Each channel is isolated from the other channel with less than a 3% channel interaction. Stimulation pulses are transformer coupled to patient connections. Each channel's output wave form is symmetrical square biphasic pulses with net zero DC component. The output pulses are "constant voltage" (+/−10%) into resistive loads from 200 Ohms to 1000 Ohms. The maximum charge of any pulse (loaded from 100 Ohms to open) does not exceed 32 μc. The intensity of both channels are always equal (+/−5%).

The IF mode of the exemplary embodiment of the present invention produces two digitally processed bipolar square waves within an area defined by four electrodes as shown in FIG. 3. Two electrodes 78a and 78b produce stimulation at a base frequency and two electrodes 79a and 79b produce stimulation at a user-selectable, pseudo frequency modulated signal formed by the microprocessor digitally simulated frequency that is different than the base signal.

The time for one cycle at 4000 Hz (waveform 150) is 1/4000 or 0.00025 seconds. The period for the 4001 waveform 152 is 1/4001 or 0.000249938 seconds. The difference between the two signals is 0.000000062 seconds (0.062 μs). This is too fast for the inexpensive microprocessors used in portable electro-therapy devices. A more expensive microprocessor could be used, but the additional expense would not be feasible for such devices. FIG. 13 illustrates how the present invention overcomes this problem.

As noted above with reference to FIG. 11, at some point the two waveforms come back together (in phase). Because the two signals are close together, the change (when not in phase) is continual, but very subtle. As shown in FIG. 13, the present invention uses a fixed signal (e.g., 4000 Hz) 150 and a pseudo signal 54 which comes back into phase with the first signal at the same time as the 4001 Hz signal 152. The pseudo signal is also a 4000 Hz signal, but with periodic shifts which cause the signal to closely mimic a 4001 Hz signal, without requiring the substantial microprocessor time required to generate the additional 4001 Hz signal. In exemplary embodiments of the invention, the shift amount is arbitrary. Preferably, the shift value is selected to fit the hardware. In exemplary embodiments, the shift amount is calculated using the following equation:

$$(K-\text{freq})/(K*\text{freq}) \quad (2)$$

where

K is a constant value used to select an appropriate shift amount and freq is the base frequency.

The time interval on which the shifts should occur is determined using the following equation:

$$(1/\text{freq})*((1/\text{freq})-(1/K))/$$
$$(1/\text{freq})-(1/(\text{freq}+\text{beat freq})) \quad (3)$$

where freq=the base frequency.

For example, if freq is 4000 and K is 4300, the shift amount is:
(4300−4000)/(4300*4000)=0.00001744 seconds or 17.44 μs.

Assuming a beat frequency of 40 Hz, the shift time is:
(1/4000)*((1/4000)−(1/4300))/(1/4000)−(1/(4000+40))= 1759 μs.

Thus, for a base frequency of 4000 Hz, a beat frequency of 40 Hz and a constant of 4300, a shift of 17.44 μs should occur every 1759 μs.

Generating signals in software rather than hardware also allows for a substantial amount of flexibility in generating a variety of signals which in turn increases the amount of available electro-therapies. For example, the above equations can be altered so that the shift occurs at varying intervals, so that the shift amount is varied or both. Signals (140 and 142 of FIG. 11) can be started at different times in the microprocessor. By varying the rate of change of the duty cycle, the rate of change per cycle can be changed. For example, the intersection of the two signals (130 of FIG. 10) can be changed. For example, the cycle shown in FIG. 10 is diamond-like in shape. The software can alter the signals so that the resulting cycle is triangular in shape or elliptical in shape, etc.

Another benefit of generating the signals in software is that the signal can be kept constant even though the power may be changing. In traditional electro-therapy devices, as, battery power begins to decrease, the output signal also becomes, weaker. By generating the output signals in software, the output can be adjusted so that the output signal remains constant even though the power level changes.

In the present invention, if both frequencies generated by an IF stimulator are viewed on an oscilloscope so that each frequency starts at the same phase, it will be seen that the higher frequency completes its cycle first. After several cycles, the higher frequency will appear to be shifted ahead of the slower frequency. After a time equal to the difference of the two frequencies, the two signals will be seen to start together again and then repeat the cycle with one frequency always shifting with respect to the other frequency.

In exemplary embodiments, the carrier frequency when performing IF stimulation is 4000 Hz, the adjustable frequency is 4001 Hz–4150 Hz when in continuous mode and 4000.6 Hz–4240 Hz when in frequency shift mode. Exemplary embodiments of the present invention include the following pulse coordination modes: continuous, 1|1, 6|6 and 6|6.

Figure 15:
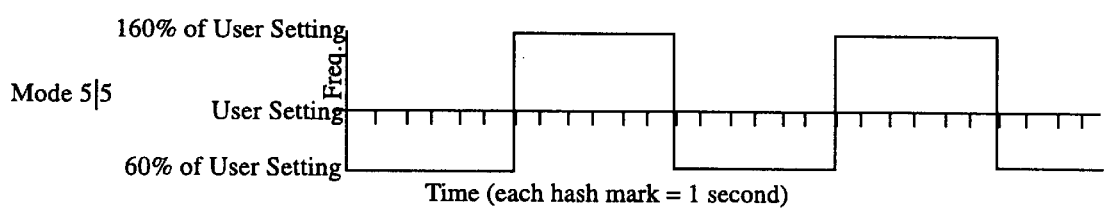
FIG. 15 illustrates an exemplary 6|6 pulse coordination waveform when the electro-therapy device of the present invention is operating in IF mode.
Figure 16:
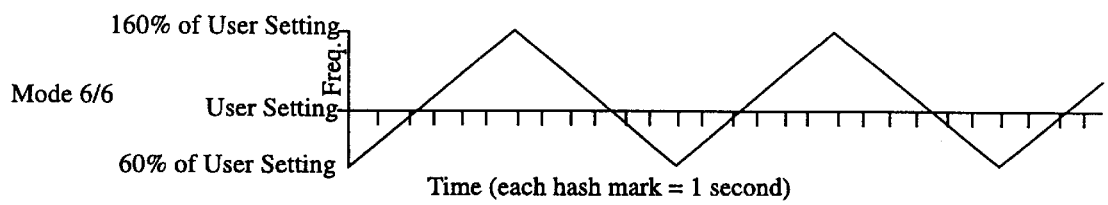
FIG. 16 illustrates an exemplary 6|6 pulse coordination waveform when the electro-therapy device of the present invention is operating in IF mode.

Continuous pulse coordination mode provides stimulation at the user selected beat frequency. 1|1 pulse coordination mode causes the beat frequency to abruptly change from 60% of the user setting to 160% of the user setting at one second intervals as shown in FIG. 14. 6|6 pulse coordination mode causes the beat frequency to abruptly change from 60% of the user setting to 160% of the user setting at six second intervals as shown in FIG. 15. 6|6 pulse mode coordination causes he beat frequency to gradually change from 60% of the user setting to 160% of the user setting over a six second period as shown in FIG. 16.

Figure 17:
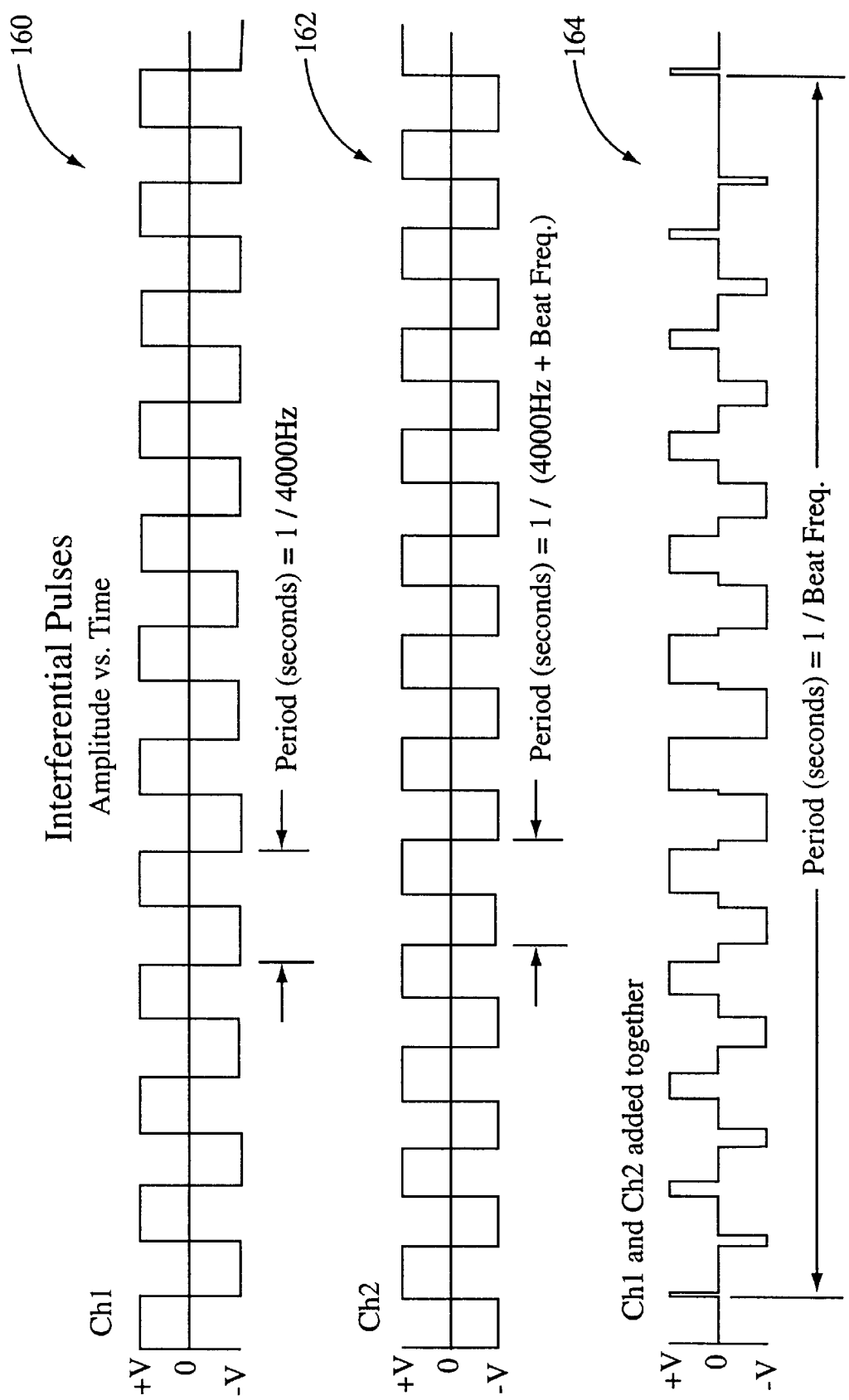
FIG. 17 is an exemplary illustration of waveforms for pre-modulated IF therapy.

In the pre-modulated IF mode, the two signals described above are added together in software to provide a constant frequency, pulse width modulated bipolar rectangular waveform through a single pair of electrodes. When the present invention is operating in the IF mode with two electrodes, a 4000 Hz square wave 160 (of FIG. 17) and a 4000 Hz plus beat frequency square wave 162 are added together inside the device. The resulting signal 164 is then provided on the channel 1 patient connection. Stimulation pulses are transformer coupled to patient connections. The output wave form is symmetrical rectangular biphasic pulses with net zero DC component. The output pulses are "constant voltage" (+/−10%) into resistive loads from 200 Ohms to 1000 Ohms. The maximum charge of any pulse (loaded from 100 Ohms to open) does not exceed 32 μc. Prior art systems use hardware to add the two signals 160 and 162 together. The present invention uses software (i.e., a microprocessor) to add the two signals 60 and 62 together. In exemplary embodiments, the equation described above is used to determine the second signal and then the two signals are added together in hardware. The adding together of signals, is well known in the art. However, it will be appreciated that traditional portable electro-therapy devices use hardware to add the signals together, whereas the present invention uses software.

Figure 18:
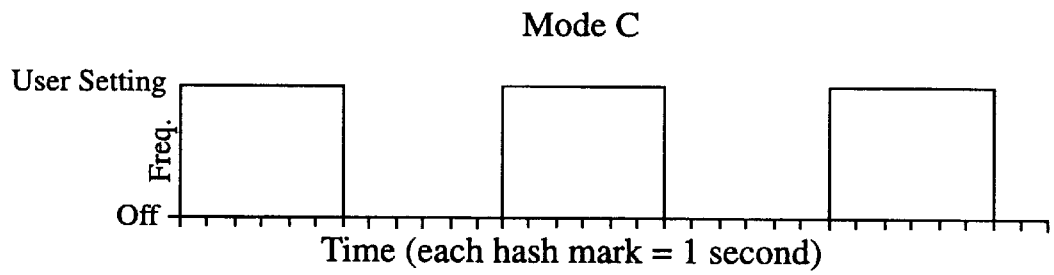
FIG. 18 illustrates an exemplary continuous pulse coordination waveform when the electro-therapy device of the present invention is operating in NM mode.
Figure 19:
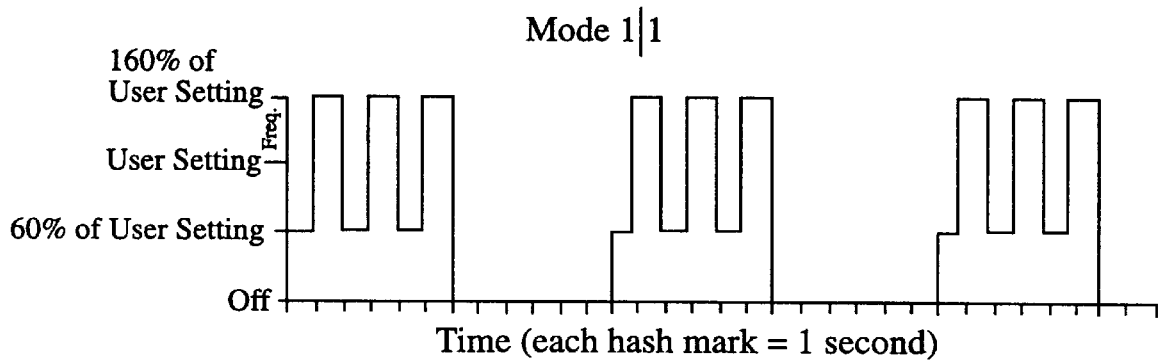
FIG. 19 illustrates an exemplary 1|1 pulse coordination waveform when the electro-therapy device of the present invention is operating in NM mode.
Figure 20:
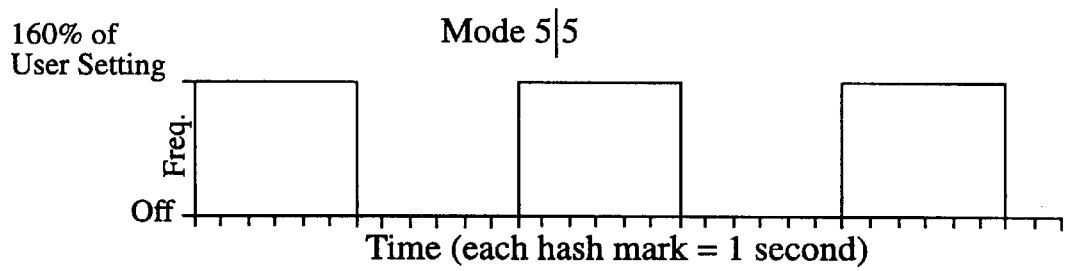
FIG. 20 illustrates an exemplary 6|6 pulse coordination waveform when the electro-therapy device of the present invention is operating in NM mode.
Figure 21:
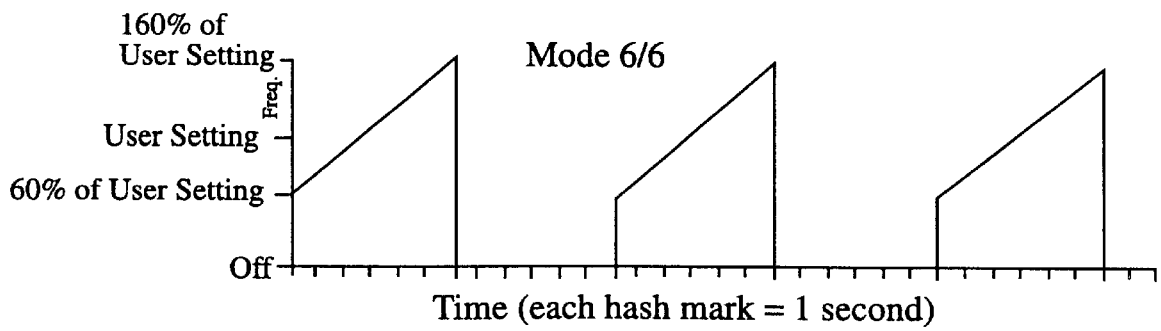
FIG. 21 illustrates an exemplary 6|6 pulse coordination waveform when the electro-therapy device of the present invention is operating in NM mode.

In the NM mode of the present invention, the IF or the pre-modulated IF waveform is gated on and off at specified rates. In exemplary embodiments of the present invention, NM stimulation has the same pulse coordination modes as IF stimulation, namely, continuous, 1|1, 6|6 and 6|6. When operating in NM mode, continuous pulse coordination mode provides stimulation to the user at the selected beat frequency in a cycle which is on for 6 seconds then turns off for six seconds as shown in FIG. 18. The 1|1 pulse coordination mode abruptly changes the beat frequency from 60% of the user setting to 160% of the user setting every second. This cycle is on for six seconds and then off for six seconds as shown in FIG. 19. In 6|6 mode, stimulation is at 160% of the beat frequency for six seconds then stimulation is off for six seconds as shown in FIG. 20. In 6|6 mode, the beat frequency gradually changes from 60% of the user setting to 160% of the user setting over a six second period. Stimulation is then off for six seconds. The cycle is then repeated as shown in FIG. 21.

In the HVPC mode, high voltage is delivered through two, three or four electrodes. The HVPC waveform is separated from all of the other waveforms by means of bi-stable relays. When the present invention is operating in the HVPC mode, twin peak, pulsed galvanic, monophasic exponential spikes are generated at the selected rate. The output pulses are "constant voltage" (+/−10%) into resistive loads from 200 Ohms to 1000 Ohms. The maximum charge of any pulse (loaded from 0 Ohms to open) does not exceed 12.5 μc. Depending on the selected parameters, the same signal is available for one or both channels. The channels share a common ground. Loading on one channel affects the other channel. The intensity of both channels is always equal (+/−5%). As with the other modes, output signals are generated using software.

Figure 22:
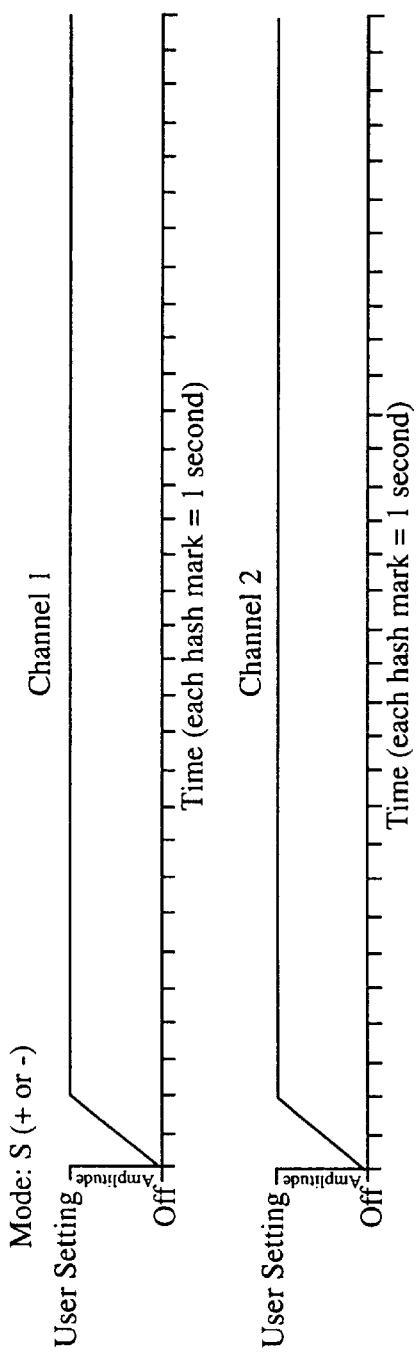
FIG. 22 illustrates an exemplary HVPC positive continuous pulse coordination mode.
Figure 23:
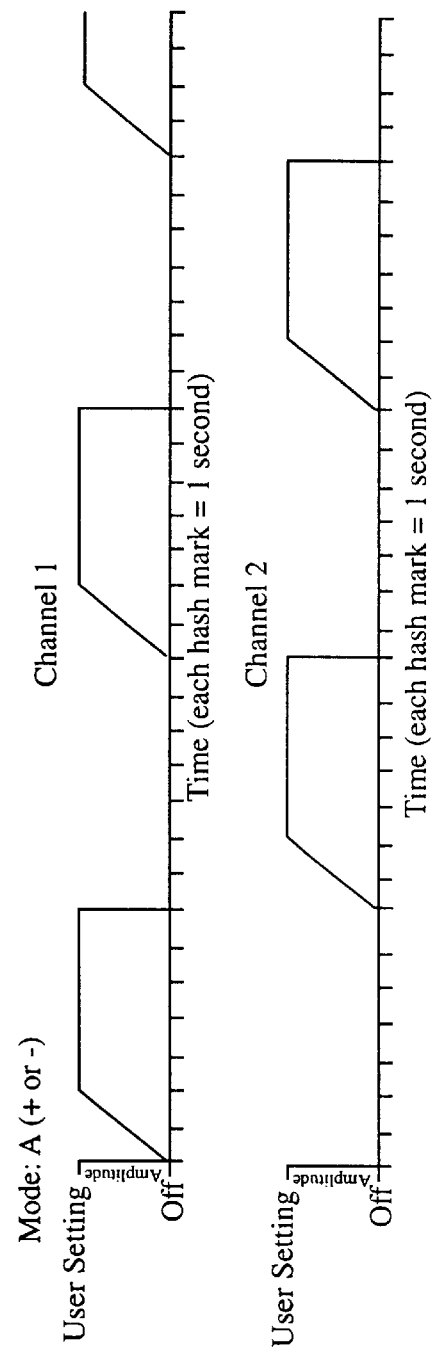
FIG. 23 illustrates an exemplary HVPC positive alternating pulse coordination mode.

HVPC pulse coordination modes may be simultaneous or alternating. FIG. 22 illustrates an exemplary positive simultaneous mode (S+). FIG. 23 illustrates an exemplary positive alternating mode. The electro-therapy device 50 of the present invention can also operate in a negative simultaneous mode (not shown) or a negative alternating mode (not shown).

Figure 24A:
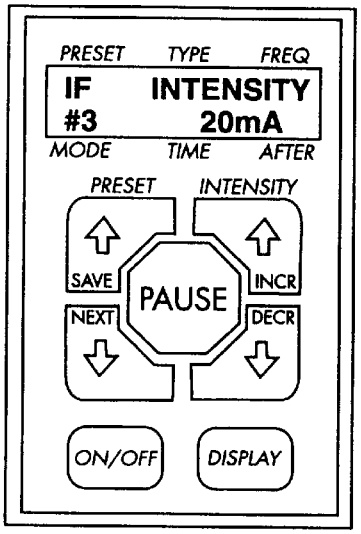
FIGS. 24A–24F illustrate exemplary user interface screen displays.
Figure 24B:
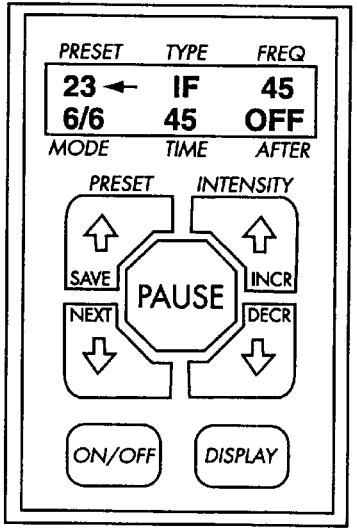
Figure 24C:
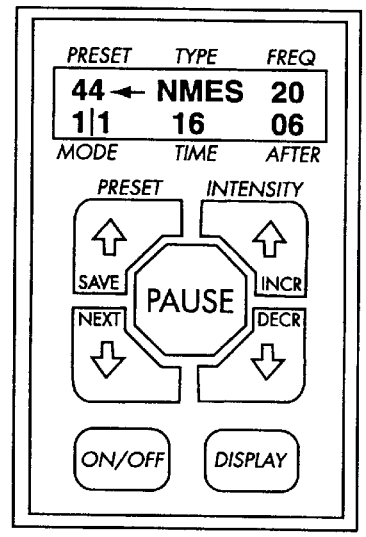
Figure 24D:
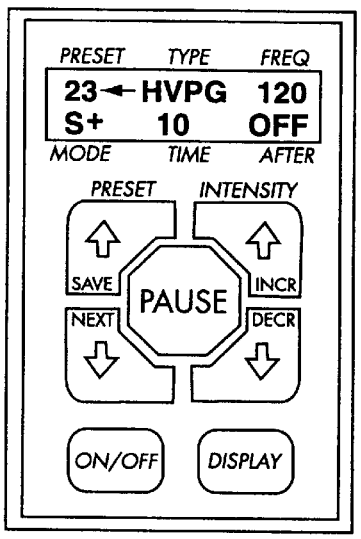
Figure 24E:
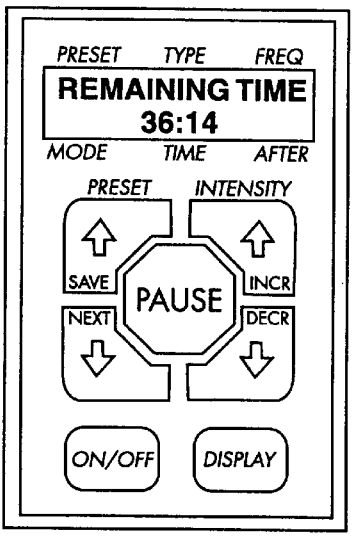

FIGS. 24A–24F are illustrations of exemplary user displays. FIGS. 24A–24D illustrate various examples of Intensity displays. In the examples, several modes have been stored (for example, by a physician). The user (e.g., patient) can then select any of the stored therapy modes. The mode selected in FIG. 24A is an IF mode which was stored as Mode #3. This mode provides therapy at 20 mA (20 milliamps). FIG. 24B is Mode #23 which is an IF mode with a 6|6 pulse coordination mode. This mode will run for 45 minutes. Upon the expiration of the specified time (45 min.), stimulation will turn off. In exemplary embodiments, when the mode has been turned on, but is not operating (e.g., Power is On, but the device has not been outputting any signals for a specified period of time), the device will automatically turn off in order to save power. FIG. 24C is mode #44 which is scheduled to provide 16 minutes of NMES therapy. After the sixteen minutes are up, the device will run the therapy defined by mode #8. Thus, a mode may include a transition to another mode or may transition to a non-operational or Off state. FIG. 3D is a display shown when the device is running stored mode #23 which is an HVPC mode scheduled to run for ten minutes. The mode is an S+ mode running at 120 Hz. Upon completion, the device transitions to an Off state.

Figure 24F:
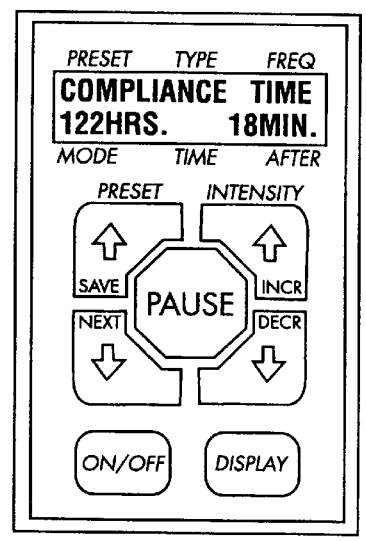

FIG. 3E is a remaining time display. For example, if the patient selected mode #23 as shown in FIG. 24B (45 minutes of IF therapy) and presses the appropriate key for displaying the remaining time after 8 minutes and 46 seconds, the display shown in FIG. 24E results showing the patient that there are 36 minutes and 14 seconds left in the 45 minutes of therapy. Preferably, this display is dynamic (i.e., continuously updated. An elapsed time display (not shown) is the opposite of the remaining time display. It shows how long the therapy (of the current mode) has been running rather than how much time is remaining for the current therapy. FIG. 24F is an exemplary screen display that a physician may use. The display of screen 24F shows the total amount of time that the patient has used the device. As described above, there are other displays that the physician uses to define and store various modes of electro-therapy.

Since software is being used to synchronize the pulses rather than independent oscillators, several other options are available. A technique known as Scanning Interference Current can be achieved by further shifts of the two frequencies. Select added frequencies can be used anywhere in the range of 0% to 200% of the two frequency sums. Other techniques not possible with the prior pulse generation are possible. For example, as described above, the signals may be started at different times, various signals can be generated by varying the duty cycle, etc.

Additional modifications and improvements of the present invention may also be apparent to those of ordinary skill in the art. Thus, the particular combination of parts described and illustrated herein is intended to represent only a certain embodiment of the present invention, and is not intended to serve as a limitation of alternative devices within the spirit and scope of the invention.

What is claimed is:

1. A portable electro-therapy device comprising:
   a. a housing;
   b. a display located on the exterior of the housing of the device;
   c. at least one keypad located on the exterior housing of the housing;
   d. at least one microprocessor located within the housing, the microprocessor being operative to generate at least a first signal with a first frequency and a first amplitude and a second signal with a second frequency and a second amplitude, wherein the second frequency and/or the second amplitude are calculated by the microprocessor according to a selected mode of electro-therapy such that the first frequency and/or amplitude can be modulated by the second frequency and/or amplitude to result in an output signal required by the selected mode of electro-therapy;
   e. an electrode jack; and
   f. at least one pair of electrodes connected to the electro-therapy device via the electrode jack, wherein the electrodes are placed in contact with a patient's skin in order to deliver output current of the output signal to the patient.

2. The device of claim 1, wherein when the mode of electro-therapy is an interferential mode, the device comprises a first pair of electrodes applying the first signal to the patient and a second pair of electrodes applying the second signal to the patient.

3. The device of claim 1, wherein the output current is in a form of:
   a. a constant output voltage; or
   b. a variable load.

4. The system of claim 3, wherein the output current is monitored.

5. The system of claim 4, wherein the output current delivered is modified based on the monitored output current if the output current type is variable load.

6. The system of claim 4, wherein the monitored output is stored.

7. The system of claim 6, wherein the stored monitored output is used to determine skin resistance.

8. The device of claim 1, further comprising a hardware mixing the first and second signals generated and calculated by the microprocessor into the output signal when the mode of electro-therapy is a pre-modulated interferential mode.

9. The device of claim 1, wherein the output signal is varied by changing a duty cycle of either the first or the second signals.

10. The device of claim 1, wherein the mode of electro-therapy can be modified by a medical professional.

11. The device of claim 10, wherein the first and second amplitudes are varied in voltages.

12. The device of claim 1, wherein the output signal is modified by varying the first or second amplitude.

13. The device of claim 1, wherein the output signal is generated by combining the first and second signals.

14. The device of claim 13, wherein the first and second signals are generated at different time.

15. The device of claim 1, further comprising a calibration device connected thereto via the electrode jack.

16. The device of claim 1, further comprising an external device to receive data via the electrode jack for processing.

17. The device of claim 1, wherein the selected mode comprises:
   a. an interferential mode;
   b. a pre-modulated interferential mode;
   c. a neuromuscular mode; and
   d. a high voltage pulse current mode.

18. The system of claim 1, wherein new modes can be created by combining existing modes.

19. The device of claim 1, further comprising a gate to switch on and off the output signal with a predetermined rate when the selected mode of electro-therapy is a neuromuscular mode.

20. The device of claim 1, wherein when the selected mode of electro-therapy is a high-voltage pulse current mode, the microprocessor is operative to generate a high voltage and the device further comprises at least an additional electrode for applying a high voltage to the patient.

21. The device of claim 20, further comprising a bi-stable relay to separate the high voltage from the first and second signals.

22. A method for providing electro-therapy to a patient using a portable electro-therapy operative to provide a plurality of modes of electro-therapy, the method comprising:
   a. accepting inputs for defining at least one mode of electro-therapy;
   b. selecting the mode of electro-therapy;
   c. based on the mode of electro-therapy, using a microprocessor to generate at least two signals and calculate at least one of the signals mixed into an output signal to be output;
   d. transmitting the output signal to at least one pair of output electrode;
   e. monitoring for a change in mode; and
   f. repeating steps c to e until the mode requires terminating transmission of the output signal.

23. The method of claim 22, further comprising a step of calibrating the portable electro-therapy device.

24. The method of claim 22, further comprising monitoring the output signal and adjusting at least one of the first and second signals according to the monitered output signal.

25. The method of claim 22, further comprising a step of storing the monitored output signal.

26. The method of claim 25, further comprising recalculating the frequency of either the first or the second signal according to the stored monitored output signal.

* * * * *